(12) United States Patent
Krasnoff et al.

(10) Patent No.: US 6,322,709 B1
(45) Date of Patent: Nov. 27, 2001

(54) AUTOMATED METHOD FOR PROCESSING BIOLOGICAL FLUID

(75) Inventors: Eric J. Krasnoff, Old Brookville; Thomas J. Bormann, Melville; Thomas C. Gsell, Glen Cove; Frank R. Pascale, Glen Cove; Vlado I. Matkovich, Glen Cove, all of NY (US)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 09/558,270

(22) Filed: Apr. 25, 2000

Related U.S. Application Data (6263) Continuation of application No. 08/949,817, filed on Oct. 14, 1997, now Pat. No. 6,106,727, which is a continuation of application No. 08/367,296, filed as application No. PCT/US93/06547 on Jul. 13, 1993, now Pat. No. 5,690,815, and a continuation-in-part of application No. 08/047,446, filed on Apr. 19, 1993, now abandoned, and a continuation-in-part of application No. 08/047,447, filed on Apr. 19, 1993, now abandoned, which is a continuation-in-part of application No. 07/912,731, filed on Jul. 13, 1992, now abandoned, and a continuation-in-part of application No. 07/912,169, filed on Jul. 13, 1992, now abandoned.

(51) Int. Cl.[7] .............................. B01D 37/00; B01D 36/00
(52) U.S. Cl. .............................. 210/739; 210/85; 210/87; 210/97; 210/143; 210/741
(58) Field of Search ................................. 210/85, 86, 87, 210/97, 109, 134, 142, 252, 257.1, 258, 416.1, 739, 741, 745

(56) References Cited

U.S. PATENT DOCUMENTS

| | | |
|---|---|---|
| Re. 33,924 | 5/1992 | Valeri . |
| 38,158 | 4/1863 | Ferris . |
| 2,579,092 | 12/1951 | Rockwell . |

(List continued on next page.)

FOREIGN PATENT DOCUMENTS

| | | |
|---|---|---|
| 0446413 | 9/1991 | (EP) . |
| 0477973 | 4/1992 | (EP) . |
| 610778 | 8/1994 | (EP) . |
| 1171612 | 10/1964 | (GB) . |
| 513153 | 1/1976 | (JP) . |
| 52-11689 | 1/1977 | (JP) . |
| 6323644 | 1/1988 | (JP) . |
| 9104088 | 4/1991 | (WO) . |
| 9117809 | 11/1991 | (WO) . |
| 9207656 | 5/1992 | (WO) . |
| 9308904 | 5/1993 | (WO) . |
| 9325295 | 12/1993 | (WO) . |

*Primary Examiner*—John Kim
(74) *Attorney, Agent, or Firm*—Leydig, Voit & Mayer, Ltd.

(57) ABSTRACT

A method for automatically processing a biological fluid is disclosed. The method includes the steps of obtaining a container having a biological fluid therein, providing a first signal and communicating with an automated control arrangement to establish flow of at least a portion of the biological fluid along a fluid flow path through a leukocyte depletion medium, providing a second signal and communicating with the automatic control arrangement to terminate flow along the fluid flow path wherein providing the second signal includes sensing the back pressure in the fluid flow path or the flow rate through the leukocyte depletion medium.

24 Claims, 28 Drawing Sheets

U.S. PATENT DOCUMENTS

| | | |
|---|---|---|
| 2,757,375 | 7/1956 | Rieutord et al. . |
| 3,000,540 | 9/1961 | Wheeler . |
| 3,030,082 | 4/1962 | Matzen . |
| 3,032,037 | 5/1962 | Huber . |
| 3,577,579 | 5/1971 | Duve et al. . |
| 3,802,432 | 4/1974 | Djerassi . |
| 3,869,924 | 3/1975 | Beezer . |
| 3,892,236 | 7/1975 | Djerassi . |
| 4,016,077 | 4/1977 | Schreiber . |
| 4,021,353 | 5/1977 | Raines et al. . |
| 4,169,681 | 10/1979 | Kato . |
| 4,303,193 | 12/1981 | Latham, Jr. . |
| 4,316,576 | 2/1982 | Cullis et al. . |
| 4,322,298 | 3/1982 | Persidsky . |
| 4,350,585 | 9/1982 | Johansson et al. . |
| 4,479,760 | 10/1984 | Bilstad et al. . |
| 4,479,761 | 10/1984 | Bilstad et al. . |
| 4,507,119 | 3/1985 | Spencer . |
| 4,588,407 | 5/1986 | Isono et al. . |
| 4,601,213 | 7/1986 | Kimball . |
| 4,608,178 | 8/1986 | Johansson et al. . |
| 4,657,542 | 4/1987 | Ohachi . |
| 4,663,032 | 5/1987 | Loos et al. . |
| 4,680,025 | 7/1987 | Kruger et al. . |
| 4,708,938 | 11/1987 | Hickenbotham . |
| 4,786,286 | 11/1988 | Cerny et al. . |
| 4,795,314 | 1/1989 | Prybella et al. . |
| 4,807,676 | 2/1989 | Cerny et al. . |
| 4,810,378 | 3/1989 | Carmen et al. . |
| 4,828,716 | 5/1989 | McEwen et al. . |
| 4,834,890 | 5/1989 | Brown et al. . |
| 4,838,861 | 6/1989 | Sharp . |
| 4,842,576 | 6/1989 | Lysaght et al. . |
| 4,880,548 | 11/1989 | Pall et al. . |
| 4,898,573 | 2/1990 | Takenaka et al. . |
| 4,923,620 | 5/1990 | Pall . |
| 4,925,572 | 5/1990 | Pall . |
| 4,943,287 | 7/1990 | Carmen . |
| 4,955,860 | 9/1990 | Ruano . |
| 4,957,637 | 9/1990 | Cornell . |
| 4,976,694 | 12/1990 | Schreibman . |
| 4,976,851 | 12/1990 | Tanokura et al. . |
| 4,985,153 | 1/1991 | Kuroda et al. . |
| 5,008,012 | 4/1991 | Hagihara et al. . |
| 5,032,288 | 7/1991 | Columbus et al. . |
| 5,035,865 | 7/1991 | Inaba et al. . |
| 5,045,185 | 9/1991 | Ohnaka et al. . |
| 5,057,429 | 10/1991 | Watanabe et al. . |
| 5,061,451 | 10/1991 | Ganshirt et al. . |
| 5,074,839 | 12/1991 | Choksi et al. . |
| 5,085,345 | 2/1992 | Wells . |
| 5,089,146 | 2/1992 | Carmen et al. . |
| 5,092,996 | 3/1992 | Spielberg . |
| 5,098,372 | 3/1992 | Jonsson . |
| 5,100,564 | 3/1992 | Pall et al. . |
| 5,102,407 | 4/1992 | Carmen et al. . |
| 5,124,030 | 6/1992 | Tanokura et al. . |
| 5,126,054 | 6/1992 | Matkovich . |
| 5,135,646 | 8/1992 | Tanokura et al. . |
| 5,139,685 | 8/1992 | De Castro et al. . |
| 5,141,490 | 8/1992 | Fujii et al. . |
| 5,147,330 | 9/1992 | Kogel . |
| 5,152,905 | 10/1992 | Pall et al. . |
| 5,154,716 | 10/1992 | Bauman et al. . |
| 5,171,456 | 12/1992 | Hwang et al. . |
| 5,174,894 | 12/1992 | Ohsawa et al. . |
| 5,178,603 | 1/1993 | Prince . |
| 5,180,504 | 1/1993 | Johnson et al. . |
| 5,207,645 | 5/1993 | Ross et al. . |
| 5,217,627 | 6/1993 | Pall et al. . |
| 5,221,474 | 6/1993 | Yokono et al. . |
| 5,229,012 | 7/1993 | Pall et al. . |
| 5,234,403 | 8/1993 | Yoda et al. . |
| 5,234,608 | 8/1993 | Duff . |
| 5,242,382 | 9/1993 | Gorsuch et al. . |
| 5,242,384 | 9/1993 | Robinson et al. . |
| 5,254,248 | 10/1993 | Nakamura . |
| 5,256,279 | 10/1993 | Voznick et al. . |
| 5,258,126 | 11/1993 | Pall et al. . |
| 5,282,982 | 2/1994 | Wells . |
| 5,322,620 | 6/1994 | Brown et al. . |
| 5,411,482 | 5/1995 | Campbell . |
| 5,433,704 | 7/1995 | Ross et al. . |
| 5,451,321 | 9/1995 | Matkovich . |
| 5,547,108 | 8/1996 | Gsell et al. . |
| 5,587,070 | 12/1996 | Pall et al. . |
| 5,690,815 | 11/1997 | Kransoff et al. . |
| 5,695,653 | 12/1997 | Gsell . |

AUTOMATED METHOD FOR PROCESSING BIOLOGICAL FLUID

This application is a continuation of patent application Ser. No. 08/949,817, filed Oct. 14, 1997, U.S. Pat. No. 6,106,727, which is a continuation of Ser. No. 08/367,296, filed Apr. 6, 1995 now U.S. Pat. No. 5,690,815, which is a 371 application of PCT/US93/06547, filed Jul. 13, 1993, which is a continuation-in-part of Ser. No. 07/912,731, filed Jul. 13, 1992, now abandoned, Ser. No. 07/912,169, filed Jul. 13, 1992, now abandoned, Ser. No. 08/047,446, filed Apr. 19, 1993, now abandoned, and Ser. No. 08/047,447, filed Apr. 19, 1993, now abandoned, each of which is incorporated by reference.

TECHNICAL FIELD

This invention relates to a system for automatically processing biological fluid and, particularly, to improved methods and apparatuses for preparing, from donated biological fluid such as whole blood, packed red cells (hereinafter PRC), a platelet suspension, usually concentrated as platelet concentrate (hereinafter PC), and plasma.

BACKGROUND OF THE INVENTION

Donated whole blood may be separated into its various components and analogous products, thereby making these different blood products available as a transfusion product. For example, a plastic collection bag containing whole blood may be centrifuged to form (1) a supernatant layer of platelet-rich plasma (PRP) and a sediment layer of packed red cells (PRC) with a buffy coat (BC) therebetween or (2) a supernatant layer of platelet-poor plasma (PPP), a sediment layer of PRC, and an intermediate layer such as buffy coat (BC). A bag containing PRP may be centrifuged to form a supernatant layer of plasma and a sediment platelet-containing layer that may be processed to form platelet concentrate (PC). Similarly, a bag containing buffy coat may be centrifuged to form a supernatant layer including platelets and a sediment layer including red cells and the supernatant layer may be separated and processed to form PC.

The separation of whole blood into components as described above may also produce leukocyte contaminated components. It is desirable to reduce the leukocyte concentration of each of the blood components by at least 70%, since the presence of leukocytes may adversely effect the storage life of the components, and/or cause undesirable effects when they are transfused into a patient. Accordingly, blood components may be leukocyte depleted, preferably by passing them through a porous medium such as a leukocyte depletion medium.

Additionally, processing of blood to provide blood components, particularly to provide leukocyte depleted blood products, may lead to the presence of gas or air, in particular oxygen, in the blood components or in the container holding the blood components, e.g., a storage container such as a satellite bag. This may lead to an impairment of the quality of the blood components and may decrease their storage life. Furthermore, the presence of air or gas in the satellite bag may present a risk factor to a patient's being transfused with a blood component.

For this reason, the separation of blood into components has substantial therapeutic and monetary value, placing additional pressure on blood banks to increase component yield and reduce costs per unit of processed biological fluid.

In view of this, there is a growing need for an efficient system and method for separating a biological fluid (e.g., whole blood) into its components. Blood bank personnel have by attempting to increase the yields of blood components in a variety of ways. However, any saving resulting from increasing the yield may be offset by the increased labor cost, if the operator of the processing system must continuously and carefully monitor the system to increase the yield.

However, increasing the yield may be counterproductive. For example, expressing more supernatant PRP from the collection container to increase the yield of platelets in the satellite container may result in the passage of red cells into the satellite container. Since red cells are undesirable, the supernatant fluid must be discarded or recentrifuged so that the red cells may be separated from the platelets.

Accordingly, the previously described methods reflect a generally unsatisfying compromise between the pressing need to maximize the yield of the historically valuable blood components such as PC, plasma, and red cells from whole blood samples, and provide for leukocyte depletion, while minimizing the effort and expense involved.

Because of the high cost and limited availability of blood components, a device comprising a porous medium used to deplete leukocytes from biological fluid should deliver the highest possible proportion of the component present in the donated blood and, at the same time, particularly when used in automated system, decrease or eliminate operator intervention during the processing. An ideal device for the leukocyte depletion of a blood component would be inexpensive, relatively small, and be capable of rapidly processing blood components obtained from about one unit or more of biological fluid (e.g., donated whole blood). Preferably, when the leukocyte depletion device is used in an automated system, the components may be separated and leukocyte depleted in, for example, less than about one hour. Ideally, automatically processing blood while utilizing this device would reduce the leukocyte content to the lowest possible level, while maximizing the yield of a valuable blood component while minimizing an expensive, sophisticated, labor intensive effort by the operator of the system. The yield of the blood component should be maximized while at the same time delivering a viable and physiologically active component—e.g., by minimizing damage due to processing, and/or the presence of air or gas.

DISCLOSURE

In the devices and methods of this invention, a biological fluid may be processed. For example, a biological fluid may be passed from one location to another and/or separated into one or more components or fractions. Typically, a biological fluid is passed through a porous medium.

In those aspects including separation of a biological fluid such as whole blood into one or more components, the separation is typically carried out within about 6 to 8 hours of the time the blood is drawn. Typically, the separated component is passed through a porous medium such as a leukocyte depletion porous medium, during this interval. Thus, in accordance with the invention, as a biological fluid is transferred from the bag containing it, leukocytes may be removed by the appropriate porous medium, and leukocyte-depleted biological fluid may be collected in a satellite bag, without, or with minimal, operator intervention. In accordance with the invention, a system is provided whereby a biological fluid such as whole blood is automatically processed to form any desired component or fraction, such as platelet-rich plasma (PRP) and PRC.

Processes and systems according to the invention may also include a red cell barrier medium that allows the passage of one component of the biological fluid, but slows or even stops the flow of red cell containing fluid and prevents the passage of red cells to the satellite bag, thereby minimizing or even eliminating the need for continuous monitoring by an operator and increasing the efficiency with which a biological fluid such as whole blood or PRP or buffy coat is separated into one or more components.

The following definitions are used in reference to the invention:

(A) Blood Product or Biological Fluid: refers to any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate (PC), platelet-rich plasma (PRP), fresh frozen plasma (FFP), platelet-free plasma, platelet-poor plasma (PPP), plasma, plasma derivatives such as cryoprecipitate, plasma fractionation products, factor concentrates; packed red cells (PRC), or buffy coat (BC); and analogous blood products derived from blood or a blood component or derived from bone marrow. The biological fluid may include leukocytes, or may be treated to remove leukocytes. As used herein, blood product or biological fluid refers to the components described above, and to similar blood products or biological fluids obtained by other means and with similar properties.

A "unit" typically refers to the quantity of biological fluid from a donor or derived from one unit of whole blood. It may also refer to the quantity drawn during a single donation. Typically, the volume of a unit varies, the amount differing patients and donations. Multiple units of some blood components, particularly platelets and buffy coat, may be pooled or combined, typically by combining 4 or more units.

(B) Porous medium: refers to at least one porous structure through which one or more blood components or biological fluids pass. For example, the PRC porous medium depletes leukocytes from a red cell containing solution or suspension, e.g., from packed red cells. The platelet or PRP porous medium refers generically to any one of the media which deplete leukocytes from the non-PRC fluids, e.g., from BC, PRP, or from PC. The red cell barrier medium as used herein is a porous medium is effective for separating the sediment red cell containing component of blood from the supernatant non-red cell containing component so that the non-red cell component may be recovered in a container without red cells entering the container, e.g., when separating PRP from PRC.

As used herein, filter assembly refers to the porous medium positioned in a suitable housing. Suitable housings include those disclosed in U.S. Pat. Nos. 4,880,548; 4,925,572; 4,923,620; 5,100,564; 5,152,905; and U.S. Ser. No. 07/846,587.

The porous media are suitable both for use with any biological fluid obtained from donated blood, including fluid obtained soon after the blood is drawn, typically within about 8 hours and for use with stored biological fluid. It may be desirable to include a pre-filter, e.g., to reduce clogging, particularly when filtered stored biological fluid.

A porous medium may be pre-formed, multi-layered, and/or may be treated to modify the surface of the medium. If a fibrous medium is used, the fibers may be treated either before or after forming the fibrous lay-up. It is preferred to modify the fiber surfaces before forming the fibrous lay-up because a more cohesive, stronger product is obtained after hot compression to form an integral filter element.

The porous element may include at least one of a prefilter element or layer and a filter element or layer. The porous medium may additionally include at least one element or layer to provide support, better drainage, and/or improved flow characteristics, such as more uniform flow distribution.

The porous medium may be configured as a flat sheet, a corrugated sheet, a web, or a membrane. The porous medium may be a depth filter, a single layer, or a composite of at least two fiber and/or membrane layers. Preferably, the porous medium forms and interference fit at its edge when assembled into the housing.

(C) Separation Medium: A separation medium refers to at least one porous medium effective for separating one component of a biological fluid from another component by passing the biological fluid in a cross flow or tangential flow manner with respect to the porous medium. The separation media according to the invention are suitable for passing at least one component of the blood product or biological fluid, particularly plasma, therethrough, but not other components of the blood product or biological fluid, particularly platelets and/or red cells.

The separation medium may be pre-formed, multi-layered, and/or may be treated to modify the surface of the medium. If a fibrous medium is used, the fibers may be treated either before or after forming the fibrous lay-up. It is preferred to modify the fiber surfaces before forming the fibrous lay-up because a more cohesive, stronger product is obtained after hot compression to form an integral filter element.

The separation medium may be configured in any suitable fashion, such as a flat sheet, a corrugated sheet, a web, hollow fibers, or a membrane. The separation medium may be a depth filter, a single layer, or a composite of at least two fiber and/or membrane layers.

MODES FOR CARRYING OUT THE INVENTION

Figure 1:
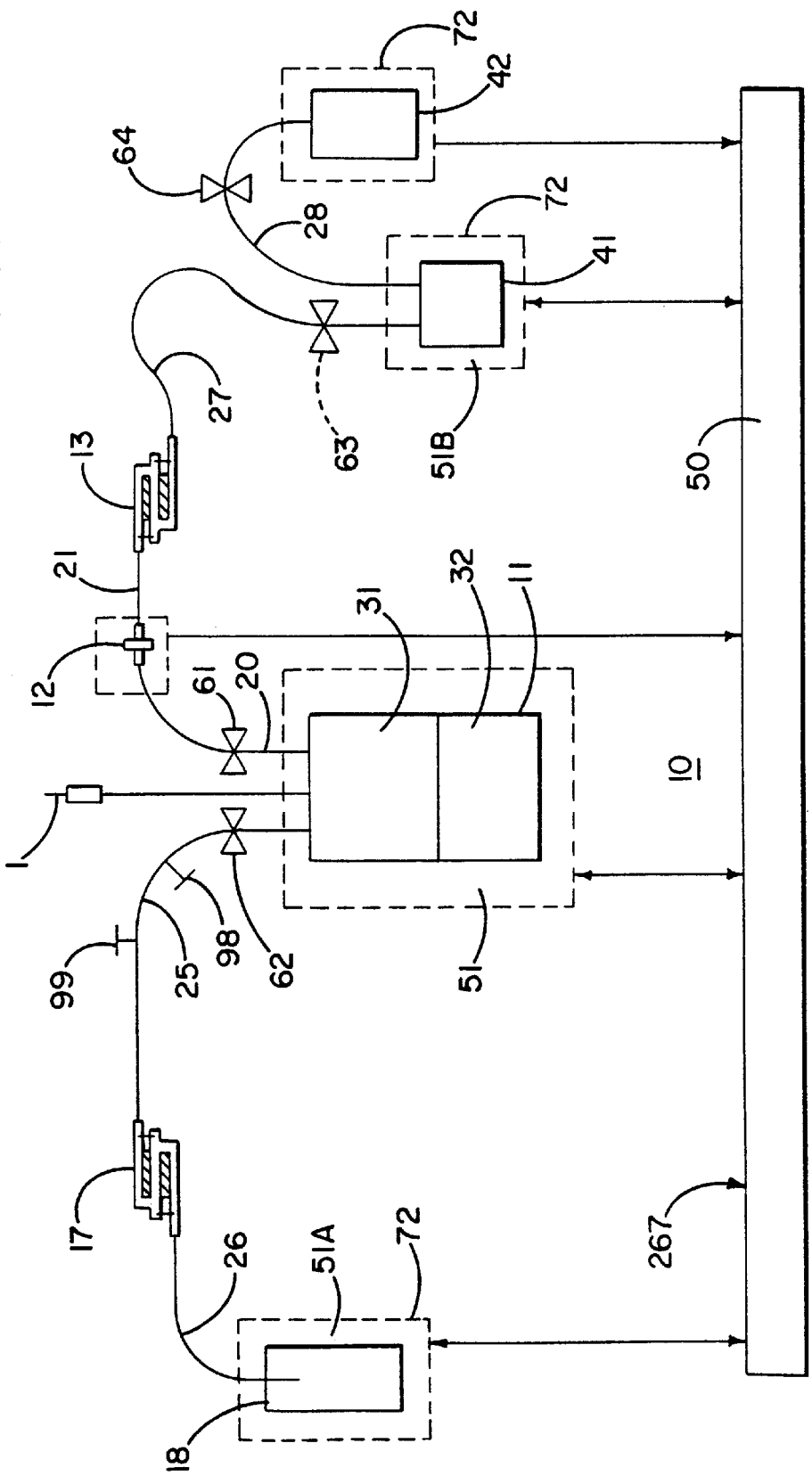
FIG. 1 is an embodiment of a biological fluid processing system according to the invention.

The present invention involves a biological fluid processing system comprising a pressure differential generator; a biological fluid processing assembly including a first container such as a collection container operatively associated with the pressure differential generator, a second container in fluid communication with the collection container, and a porous medium interposed between the collection container and the second container; and an automated control arrangement coupled to at least one of the pressure differential generator and the biological fluid processing assembly to control flow between the collection container and the second container.

In a preferred embodiment, the biological fluid processing assembly includes a first porous medium, comprising at least one of a leukocyte depletion medium, a red cell barrier medium, and a combined leukocyte depletion red cell barrier medium; and/or a second porous medium, which may be a leukocyte depletion medium which may, optionally, include a microaggregate filter element and/or a gel pre-filter element.

The invention also includes a method for automatically processing a biological fluid comprising expressing a biological fluid from a first container to at least one porous medium such as a leukocyte depletion medium, a red cell barrier medium, a red cell barrier leukocyte medium, and a separation medium. The method may also include processing the fluid through additional containers, flow paths, and porous media, and the system may be designed to process more than one separate unit at the same time.

Preferably, the method comprises expressing a biological fluid from a first container to a first porous medium comprising a red cell barrier medium; and expressing a biological fluid from the first container to a second porous medium.

The invention includes a method for automatically processing a biological fluid comprising:
a) placing a container of biological fluid into an enclosed chamber of a differential pressure generator; b) supplying a signal from an automated control arrangement to the differential pressure generator; and c) in response to the signal, varying pressure within the chamber to establish fluid flow into or out of the container.

The invention also includes a method for automatically processing a biological fluid comprising:
a) placing a container of biological fluid into an enclosed chamber of a differential pressure generator; b) supplying a signal from an automated control arrangement to the differential pressure generator; and c) in response to the signal, varying pressure within the chamber to establish fluid flow into or out of the container.

A method according to the invention includes automatically processing a biological fluid comprising:
a) establishing flow of a first portion of a biological fluid along a first fluid flow path to at least one of a leukocyte depletion porous medium, a red cell barrier medium, or a combined leukocyte depletion red cell barrier medium; b) generating a signal indicative of the separation of the first portion of the biological fluid and a second portion, and supplying the signal to an automated control arrangement; and c) in response to the signal, terminating flow through the first fluid flow path.

A method for processing a biological fluid according to the invention comprises separating a biological fluid into a supernatant portion and a sediment portion; and passing at least one of the supernatant portion and the sediment portion through at least one porous medium, wherein said passing includes initiating, monitoring, and terminating flow of the portions by an automated control arrangement.

The invention also involves a method for automatically processing a biological fluid separated to form a supernatant layer and a sediment layer comprising, passing the supernatant layer of the separated biological fluid through a first porous medium, the first porous medium comprising at least one of a leukocyte depletion medium, a red cell barrier medium, and a combined leukocyte depletion red cell barrier medium; and passing the sediment layer of the separated biological fluid through a second porous medium, the second porous medium comprising a leukocyte depletion medium.

The invention also may involve separating the biological fluid into three layers—the supernatant and sediment layers are noted above, and an intermediate layer. In the embodiments of the invention in which an intermediate layer or zone is formed, the intermediate layer or zone, typically buffy coat, can be further processed into a second supernatant layer and a second sediment layer. The second supernatant layer may then be passed through a third porous medium comprising at least one of a leukocyte depletion medium, a red cell barrier medium, and a combined leukocyte depletion red cell barrier medium. The second sediment layer may be passed through a fourth porous medium comprising a leukocyte depletion medium.

Exemplary automated biological fluid collection and processing systems are shown in FIGS. 1, 2, 17, 18, 23, and 31. A system according to the invention may comprise a pressure differential generator 51, e.g., an expressor, or the like, suitable for inducing fluid flow from a container such as a collection container 11 to other parts of the system, or inducing flow from other parts of the system to collection container 11. The pressure differential generator is operatively associated with a biological fluid processing assembly, an example of which is shown as 10 in FIG. 1.

Figure 3:
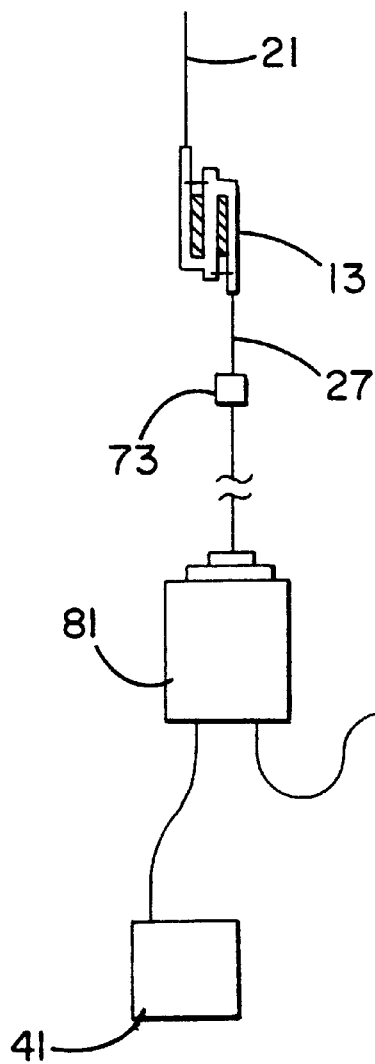
FIG. 3 is an optional biological fluid processing assembly segment which includes a separation medium.
Figure 31:
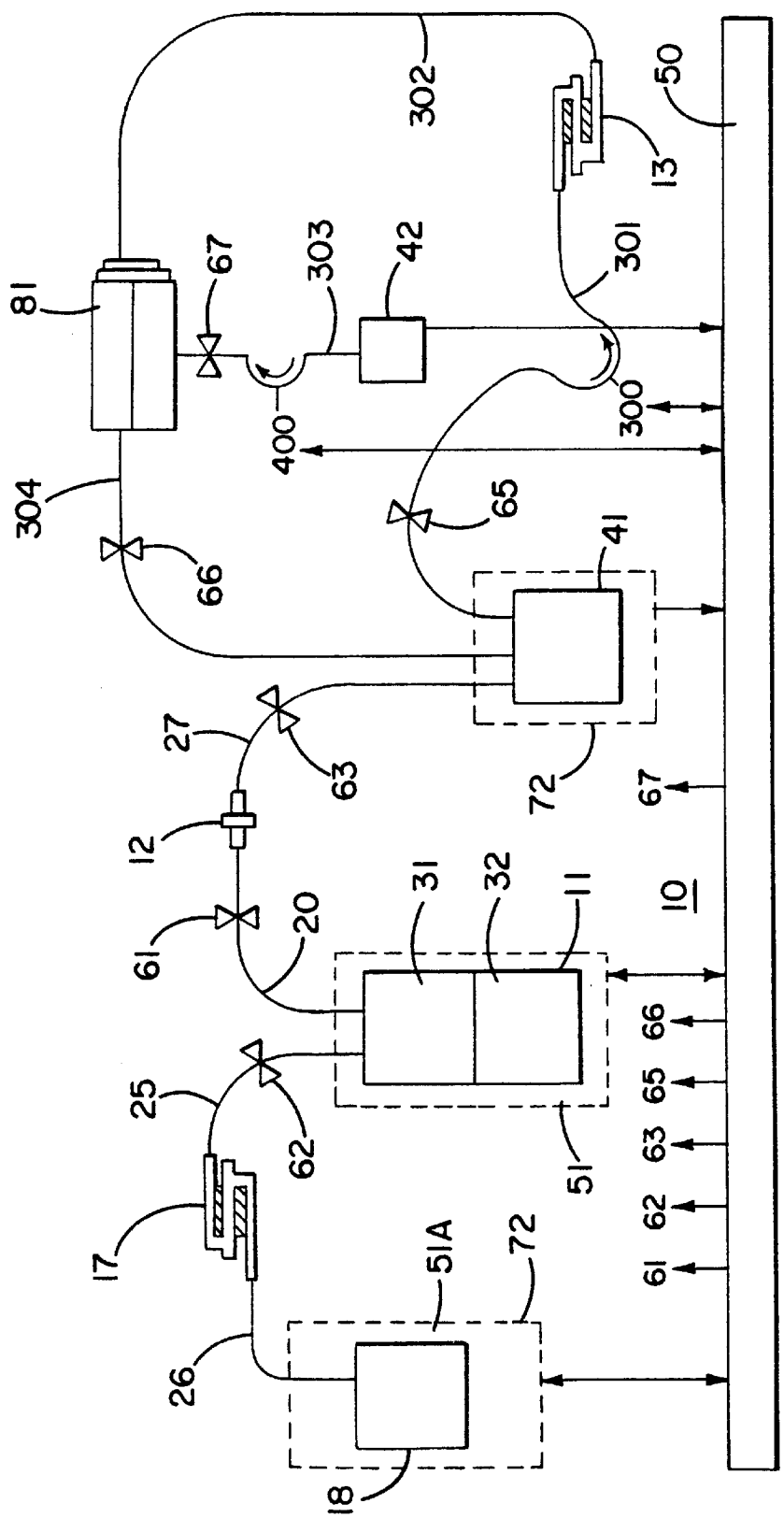
FIG. 31 is another embodiment of a biological fluid processing system according to the invention.

The individual parts which constitute a biological fluid processing assembly 10 may vary according to an intended use. In the illustrated embodiments, the biological fluid processing assembly 10 may comprise a first container or collection bag 11; a needle or the like 1 to be inserted into or connected to the donor; a red cell barrier assembly 12; a first leukocyte depletion assembly 13, preferably suitable for removing leukocytes from a platelet-containing solution or suspension, e.g., PRP; a second container (e.g., a first satellite bag) 41 suitable for receiving and/or storing a platelet-containing solution or suspension, for example; an optional fourth container (e.g., a third satellite bag) 42 suitable for receiving and/or storing platelet concentrate or plasma, for example; a second leukocyte depletion assembly 17, preferably suitable for removing leukocytes from a red cell containing solution or suspension, e.g., PRC; and a third container (e.g., a second satellite bag) 18 suitable for receiving and/or storing a red cell containing solution; and at least one flow control device, 61, 62, 63, 64. In other embodiments, for example as illustrated in FIGS. 3 and 31, the biological fluid assembly 10 may include a separation assembly 81, preferably a non-centrifugal separation device. The biological fluid processing assembly 10 may include at least one gas control element such as a gas inlet 99, 74, and a gas outlet 98, 73, 74, as exemplified in FIGS. 1, 3 and 4.

Each of the assemblies or containers may be in fluid communication through conduits 20, 21, 25, 26, 27 or 28. A seal, valve, clamp, pinch clamp, or transfer leg closure or cannula may also be positioned in or on the tubing or in the collection and/or satellite bags. In accordance with the present invention, the assemblies, containers, flow control device, gas control elements, and conduits may be previously connected in a closed, sterile manner, or segments of the system may be inserted into a closed system in a sterile manner.

In accordance with the present invention, processing a biological fluid through the system can be automated by coupling an automated control arrangement to the biological fluid processing assembly 10 and/or to the pressure differential generator 51. The individual parts which constitute an automated control arrangement may vary according to an intended use. In the illustrated embodiments, the automated control arrangement may comprise a control unit 50, typically a microprocessor controller, and one or more sensors, and may be coupled to at least one of the pressure differential generator 51 and the biological fluid processing assembly 10 to control flow between the first container 11 and another container 41 and/or 18.

Each of the components of the assembly will now be described in more detail below.

Movement of the biological fluid through the system is effected by maintaining a pressure differential between the container holding the biological fluid, e.g., the collection container, and the destination of the biological fluid (e.g., a container such as a satellite bag). Exemplary means of establishing this pressure differential may be by a mechanical member such as a plate bearing directly against the collection container, an expressor such as a mechanical, pneumatic or hydraulic expressor, gravity head, applying pressure to the collection bag by hand or with a pressure cuff, by placing the other container (e.g., satellite bag) in a chamber (e.g., a vacuum chamber) which establishes a pressure differential between the collection bag and the other container, or by a pump such as an in-line pump.

In accordance with the invention, expressors which generate substantially equal pressure over the entire collection bag may be used. Also included are expressors which shake or agitate the biological fluid, and expressors which are capable of rotating on an axis, e.g., so that the upper discharge conduit becomes a lower discharge conduit. Alternatively, the collection container may be capable of rotating along its horizontal axis in order to change the relative position of the discharge conduit.

An exemplary pressure differential generator may include a housing defining a chamber suitable for positioning a container therein. The housing or chamber may be in fluid communication with a pressure regulating machanism suitable for varying the fluid pressure applied to the outside of the container positioned in the chamber. In a preferred embodiment, the pressure differential operator includes an enclosed housing defining a chamber such that the pressure within the chamber may be increased or decreased substantially evenly over the entire outside of the container.

The pressure differential generator may also be arranged to resist distortion of the container and to promote uniform and complete expression of fluid from the container. The pressure differential generator may also be arranged to mix the contents of the container, e.g., the PRC and an additive or preservative solution.

The biological fluid processing assembly may include any number and combinations of assemblies porous media, flow control devices, gas control elements, containers, and conduits interconnecting them. One skilled in the art will recognize that the invention as described here may be reconfigured into different combinations. Exemplary biological fluid processing assemblies are disclosed in U.S. Pat. No. 5,100,564 and International Publication No. WO 92/07656.

In accordance with the invention, the conduits, assemblies, porous media, gas control elements, containers, and flow control devices which constitute a biological fluid processing assembly may be arranged to define different flow paths for biological fluid and/or gas. For example, when whole blood is processed, the PRP may flow along a first flow path, e.g., through a red cell barrier assembly (if present), a PRP leukocyte depletion assembly, and into a satellite bag (e.g., a second container). Similarly, the PRC may flow along a second flow path, e.g., through the PRC leukocyte depletion assembly, and into a satellite bag (e.g., a third container). Since independent flow paths may be present, included within the scope of the present invention is the concurrent or sequential passage of separate biological fluids (e.g., PRP and PRC) through the biological fluid processing assembly.

The containers and conduits which are used in the biological fluid processing assembly may be constructed of any material compatible with a biological fluid and gas, such as whole blood or a blood component. Preferred embodiments may be capable of withstanding a centrifugation and sterilization environment. A wide variety of these containers are already known in the art. For example, blood collection and satellite bags are typically made from plasticized polyvinyl chloride, e.g. PVC plasticized with dioctylphthalate, diethylhexylphthalate, or trioctyltrimellitate. The bags may also be formed with polyolefin, polyurethane, polyester, and polycarbonate.

The conduit may be any tubing or means which provide fluid communication between the containers, and is typically made from the same flexible material as is used for the containers, preferably plasticized PVC. The conduit may be compatible with an automatic sealing system. It is intended that the present invention is not limited by the type of material used to construct the containers or the conduits which connect the containers.

The containers and/or conduits may be modified according to an intended use. For example, the containers may include at least one internal passageway to allow fluid to flow to or from a particular portion of the container located near the passageway. The container and/or conduit may be segmented, compartmentalized and/or enlarged, typically to provide for isolation of a portion of the biological fluid, e.g., for sampling.

The conduit may extend into the interior of the container. There may be a number of tubes providing fluid communication to any individual container, and the tubes may be located in a number of ways. For example, there may be at least two tubes located at the top of the collection bag, or at the bottom of the bag, or a tube at each end of the bag, or a tube extending from an intermediate portion of the bag. Included within the scope of the present invention are single inlet and/or discharge tube containers (upper and lower); two inlet and/or discharge tubes (upper, lower, and both); three tubes (upper, lower, and/or intermediate), and variations on any of these configurations. Also included within the scope of the present invention is the use of at least one clamp associated with a container for physically separating a layer within the container from another layer.

A flow control device, such as a seal, valve, clamp, pinch clamp, roller, transfer leg closure, or the like is typically located in or on the conduits and/or containers. In accordance with the invention, a flow control device may be positioned on or in any or all of the conduits and/or containers in order to facilitate a desired function, i.e., establishing a desired flow path for biological fluid or gas. Preferably, the flow control device may be controlled, e.g., opened and closed, in response to the automated control arrangement. It is intended that the present invention should not be limited by the number, placement, or use of such flow control devices.

The porous media for removing leukocytes from a biological fluid may be any media which effectively removes leukocytes without having a deleterious effect on the biological fluid passing therethrough. In an embodiment of the invention, a porous medium for use with a biological fluid such as a non-red cell containing layer (e.g., PRP) may comprise a medium disclosed in U.S. Pat. No. 4,880,548. In a preferred embodiment of the invention, a porous medium for use with a biological fluid such as a red cell containing layer (e.g., PRC), may comprise the type of media disclosed in U.S. Pat. No. 4,925,572 and U.S. Pat. No. 4,923,620, as well as U.K. Patent Application No. GB 2,231,282A.

Figure 17:
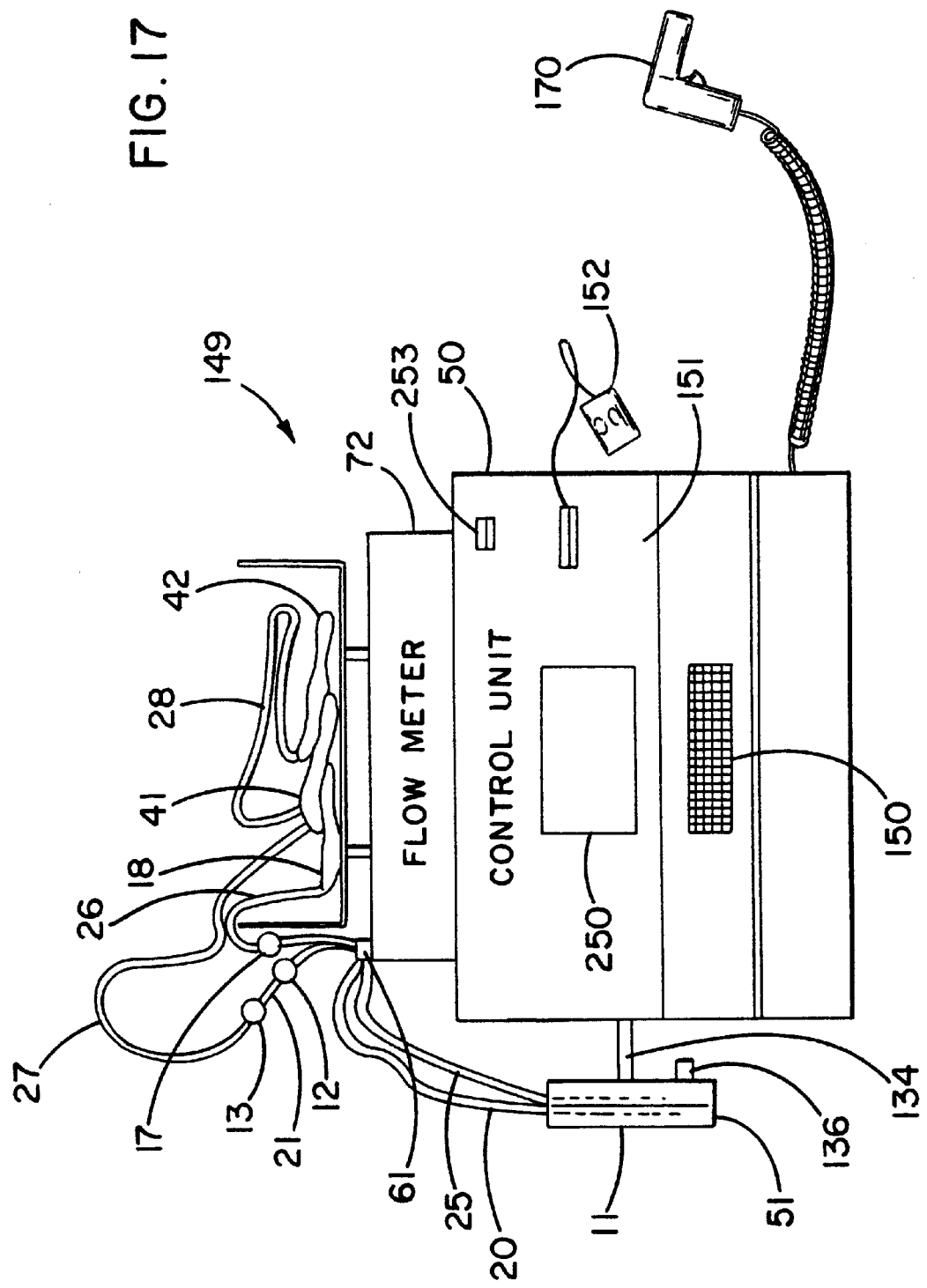
FIG. 17 is a front view of an embodiment of a biological fluid processing system according to the invention.

In accordance with the invention, the conduits, filter assemblies, porous media and containers may be positioned according to the intended use. For example, as shown in FIG. 17, satellite bags 18, 41 and 42 may rest on a flow meter 72. In other embodiments (not shown) at least one support means including but not limited to a tray, a scale, a bracket, a hook and a chamber may be used to support or hold at least one container bag in a desired position and/or at a desired location. For example, the support means may hold the satellite bag in an inverted or an upright position and/or at a different level than the collection bag 11. The support means may also be suitable for weighing at least one container.

A red cell barrier medium, in accordance with the present invention, comprises a porous medium that allows the separation of a non-red cell containing biological fluid, such as a suspension of platelets and plasma, from a red cell containing biological fluid. The red cell barrier medium prevents the red cell containing biological fluid from entering a container such as a satellite bag or a receiving container downstream of the barrier medium The red cell barrier medium allows the non-red cell containing fluid to pass therethrough but significantly slows or effectively stops the flow of biological fluid as the red cell containing fluid approaches the barrier medium. Accordingly, a supernatant non-red cell containing fluid such as a platelet suspension may be separated from a sediment red cell containing fluid by passing the platelet suspension through a red cell barrier medium. Accordingly, a supernatant non-red cell containing fluid such as a platelet suspension may be separated from a sediment red cell containing fluid by passing the platelet suspension through the red cell barrier medium. For example, the red cell barrier medium may allow a platelet-containing fluid to pass therethrough, abruptly stopping flow when red blood cells block the medium.

By slowing the flow of the biological fluid, the barrier medium allows the operator or the automated control arrangement to manually stop the flow to prevent the red cell containing biological fluid from entering a container such as a satellite bag or a receiving container downstream of the barrier medium. This embodiment of the invention allows the operator or the automated control arrangement more time to intervene and stop the flow. For example, a supernatant platelet-containing fluid may flow through the red cell barrier medium at an initial rate of about 15 ml/min, but the flow may decrease to about 5 ml/min as a sediment red cell containing fluid approaches the medium. A reduction in flow, e.g., a 33% reduction, may provide the operator sufficient time to stop the flow at the appropriate time. In some circumstances, for example, when platelet-containing fluid is expressed from a plurality of separate bags at approximately the same time, this reduction in flow allows the operator to process a greater number of containers more efficiently.

A principal function of the red cell barrier medium is to separate a red cell containing fraction of a biological fluid from a non-red cell containing fraction. The red cell barrier medium may act as an automatic "valve" by slowing or even stopping the flow of the red cell-containing biological fluid. In some embodiments, the automatic valve function may quickly or instantly stop the flow of the red cell-containing biological fluid, thereby obviating the need for the operator to monitor this step.

The valve-like action is not well understood, but it is believed that flow is slowed or stopped due to aggregation in or on the medium of one or more constituents in the biological fluid. For example, at the present time, it is believed that as the non-red cell containing biological fluid passes through the medium, leukocytes are depleted from this fluid. These leukocytes appear to accumulate in or on the medium, but the remainder of the non-red cell containing fluid typically flows through the medium. However, once red cells directly or indirectly contact the medium, e.g., directly contact the medium or contact the leukocytes which, in turn, may directly contact the medium, flow through the medium slows significantly, even stops. Without intending to be limited to any particular explanation for the mechanism of this valve-like action, it is presently believed that the slowing or stoppage of flow may reflect aggregation of the red cells alone and/or in combination with leukocytes, forming a barrier which prevents or blocks further flow through the porous medium. It may be that other factors, such as the zeta potential, the CWST, and/or other characteristics of the fibers or the porous medium may contribute to the valve-like action.

In one embodiment of the invention, the leukocyte depletion efficiency of the red cell barrier medium is increased, and so the red cell barrier medium may also function as a leukocyte depletion medium. Exemplary red cell barrier media and red cell barrier/leukocyte depletion media are disclosed in U.S. Pat. Nos. 5,100,564 and 5,152,905; U.S. Ser. Nos. 07/846,587 and 07/896,580; and International Publication No. WO 91/04088.

In another exemplary configuration, the biological fluid processing assembly may include a separation assembly 81, preferably a non-centrifugal separation assembly, as shown in FIGS. 3 and 31.

This embodiment of the present invention involves the separation of one or more components from a biological fluid without subjecting the biological fluid to centrifugation. In another aspect, one or more components may be separated without subjecting the biological fluid to hard spin centrifugation. In accordance with the present invention, a biological fluid, particularly whole blood or PRP, may be exposed to a separation medium suitable for passing at least one component of the biological fluid, particularly plasma, therethrough, but not other components of the biological fluid, particularly platelets and/or red cells. Clogging of the separation medium by these other components is minimized or prevented. Preferably platelet adhesion to the separation medium is minimized.

An embodiment of a separation assembly which includes a separation medium may be considered a non-centrifugal separation assembly. A biological fluid may be passed through the non-centrifugal separation assembly where it may be separated into components which may be separately collected in containers.

In accordance with the invention, a biological fluid may be processed to form a supernatant layer and a sediment layer, and the supernatant layer (e.g., PRP) may be passed through at least one filter assembly such as a leukocyte depletion filter assembly, a red cell barrier filter assembly, or a red cell barrier/leukocyte depletion filter assembly, and then passed through a non-centrifugal separation assembly where it may be processed and separated into components, which may be separately collected in container 41 and container 42. In a preferred embodiment, if the supernatant fluid is PRP, it may be passed through a red cell barrier filter assembly 12 or a red cell barrier filter/leukocyte depletion filter assembly, and then passed through a non-centrifugal separation assembly it may be separated into a plasma rich fluid, e.g., plasma, and a plasma-depleted fluid, e.g., a platelet containing fluid as platelet concentrate, as the PRP passes through the non-centrifugal separation device. The sizes, nature, and configuration of the present invention device can be adjusted to vary the capacity of the device to suit its intended environment, and may be suitable for recirculating biological fluid through the separation assembly. Additionally, multiple separation medium assemblies may be used. Exemplary separation media and assemblies include but are not limited to those disclosed in International Publication Nos. WO 92/07656 and WO 93/08904.

In a preferred embodiment, the present invention may utilize cross or tangential flow to the separation medium. For example, a differential pressure generator such as a peristaltic pump 300 may be used to direct a biological fluid such as PRP tangentially to the surface of the separation medium such that the plasma-rich fluid, e.g., plasma passes through the separation medium, and the plasma-depleted fluid, e.g., a platelet-containing fluid, passes tangentially across the separation medium.

The plasma depleted fluid passing tangentially across the separation medium may be repeatedly recirculated through the separation assembly. Typically, recirculation is repeated until the plasma depleted fluid in the satellite bag contains a pre-determined amount or concentration of the desired component, e.g., platelets.

In a more preferred embodiment, passing biological fluid through the separation assembly may also include providing a reverse pressure differential across the separation medium, e.g., by creating a backflow across the medium. Without intending to be limited to any explanation of the mechanism, it is presently believed that a reverse pressure differential may provide for minimizing platelet adhesion to, or contact with, the separation medium. The reverse pressure differential may also provide for minimizing clogging of the separation medium by blood components such as platelets and/or red cells.

Typical devices for creating reverse pressure differential include, but are not limited to at least one of a pump such as a peristatic pump, a valve such as a check valve and the like.

The number, type and location of the devices which create the reverse pressure differential as well as the manner of creating the pressure differential may be varied according to an intended use. In one embodiment of the invention, as exemplified in FIG. 31, at least one reverse differential pressure generator such as a peristaltic pump 400, may be located between the separation assembly 81 and a container such as a satellite container 42, to provide for backflow across the separation medium. As shown in FIG. 3, the biological fluid processing assembly may also include conduits 301, 303, and 304, as well as flow control device 65, 66, and 67.

In a preferred embodiment, the reverse differential pressure creating device provides for pulsed backflow across the separation medium in the separation device 81 while there is continuous transverse or cross flow across the separation medium. As used hereinafter, the term "pulsed" refers to non-continuous, periodic, or intermittent backflow across the separation medium.

In the embodiment illustrated in FIG. 31, pulsed backflow may be provided by a reverse pressure differential generator 400, while transverse flow may be provided by a pressure differential generator 300.

With respect to the reverse differential pressure generator 400, a peristaltic pump providing less than a 100% duty cycle may be utilized to provide for pulsed backflow.

Figure 32:
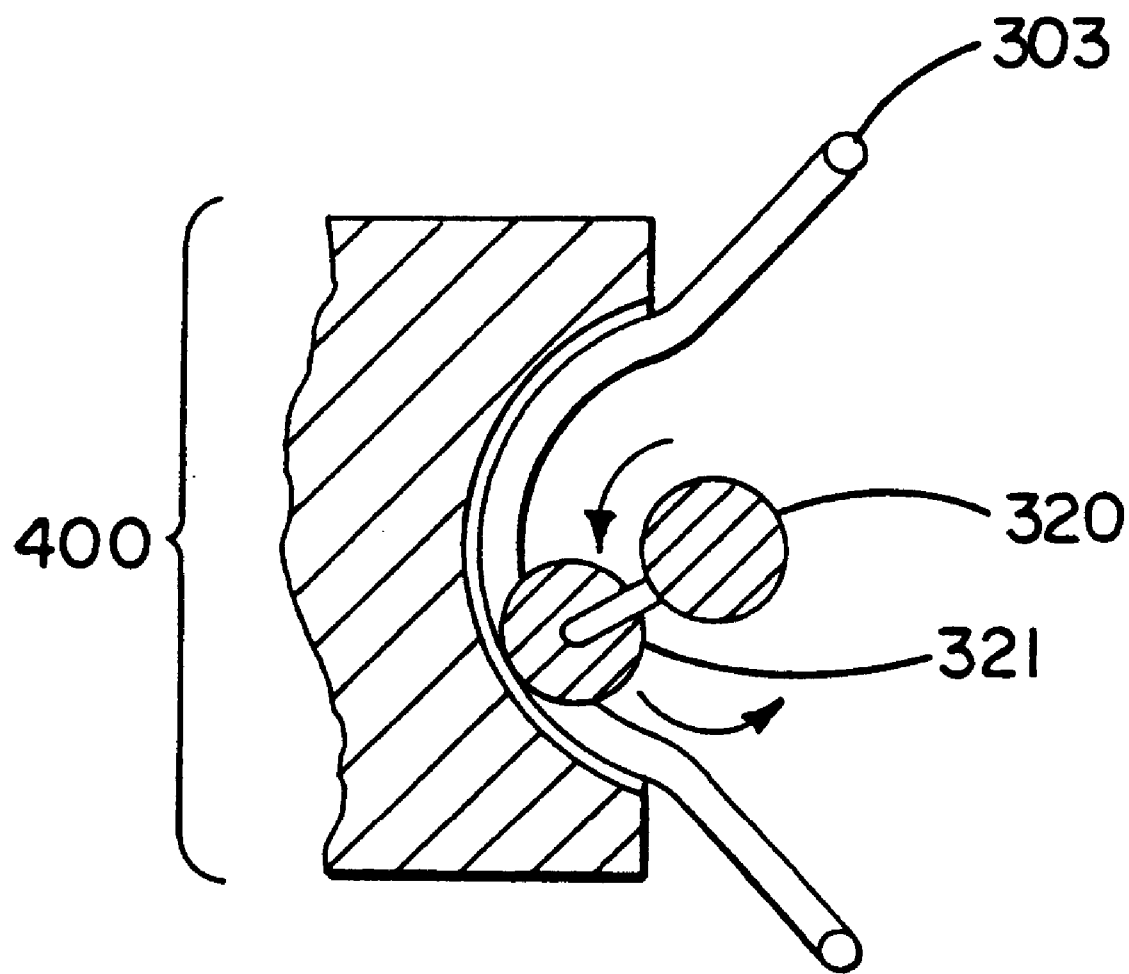
FIG. 32 is an explanatory view of an embodiment of a reverse pressure differential generator according to the invention.

Typically, a duty cycle of less than about 75%, more preferably, less than about 50%, may be utilized. As shown in FIG. 32, a peristaltic pump 400 including a rotor 320 utilizing a single roller 321 may be used. Multi-roller peristaltic pumps may also be used, preferably after removing at least one roller.

In contradistinction, differential pressure generator 300 should preferably provide continuous, rather than pulsed, flow. Accordingly, if differential pressure generator 300 is a peristaltic pump, the duty cycle should be greater than about 75%. Thus, while differential pressure generators 300 and 400 may both comprise peristaltic pumps, in a preferred embodiment, 300 may be a multi-roller peristaltic pump, while 400 may be a single roller peristaltic pump as described above.

In accordance with the invention, the biological fluid processing system may include at least one gas control element to allow gas, such as air, to be moved or displaced as desired during processing. For example, a gas control element may be used to remove gas from the system, to separate or displace gas from one part of the system to another part, to introduce gas into a biological fluid processing system or to separate gas from the biological fluid being processed. Exemplary gas control elements include, but are not limited to, at least one of a gas inlet, a gas outlet, a gas collection and displacement loop, a gas container, a bypass conduit and a conduit which extends into the biological fluid in the container, or combinations of any of these. Gs control elements may be used together or separately. For example, vents such as a gas inlet and a gas outlet may be used together in connection with at least one assembly, porous medium, or container in the system, or they may be used separately.

As used herein, gas refers to any gaseous fluid, such as air, sterilized air, oxygen, carbon dioxide, and the like; it is intended that the invention is not to be limited to the type of gas used.

It may be desirable to displace or remove gas, since, for example, gas ahead of a column of biological fluid may clog or impair the function of a porous medium such as a leukocyte depletion porous medium used to treat the biological fluid. Also, gas in the receiving container may effect the processed biological fluid stored in that container. Accordingly, an aspect of the instant invention provides means and methods for minimizing the volume of gases that remain in, or in contact with a biological fluid during storage.

It may be desirable to displace, introduce and/or remove gas to maximize the recovery of a biological fluid retained or entrapped in various elements of the biological fluid processing system as this valuable fluid would otherwise be lost. For example, under typical conditions, using a typical device, the biological fluid will drain through the system until the flow is stopped, leaving some of the fluid in the system. In one embodiment of the invention, the retained fluid may be recovered by using at least one gas control element, for example, a gas collection and displacement loop, a gas container, at least one gas inlet and/or at least one gas outlet.

Figure 4:
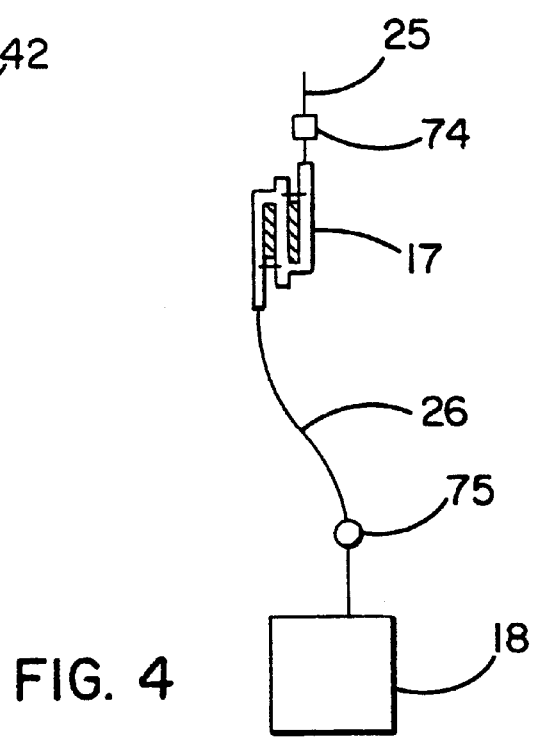
FIG. 4 is an optional biological fluid processing assembly segment which includes a gas inlet and a gas outlet.
Figure 5:
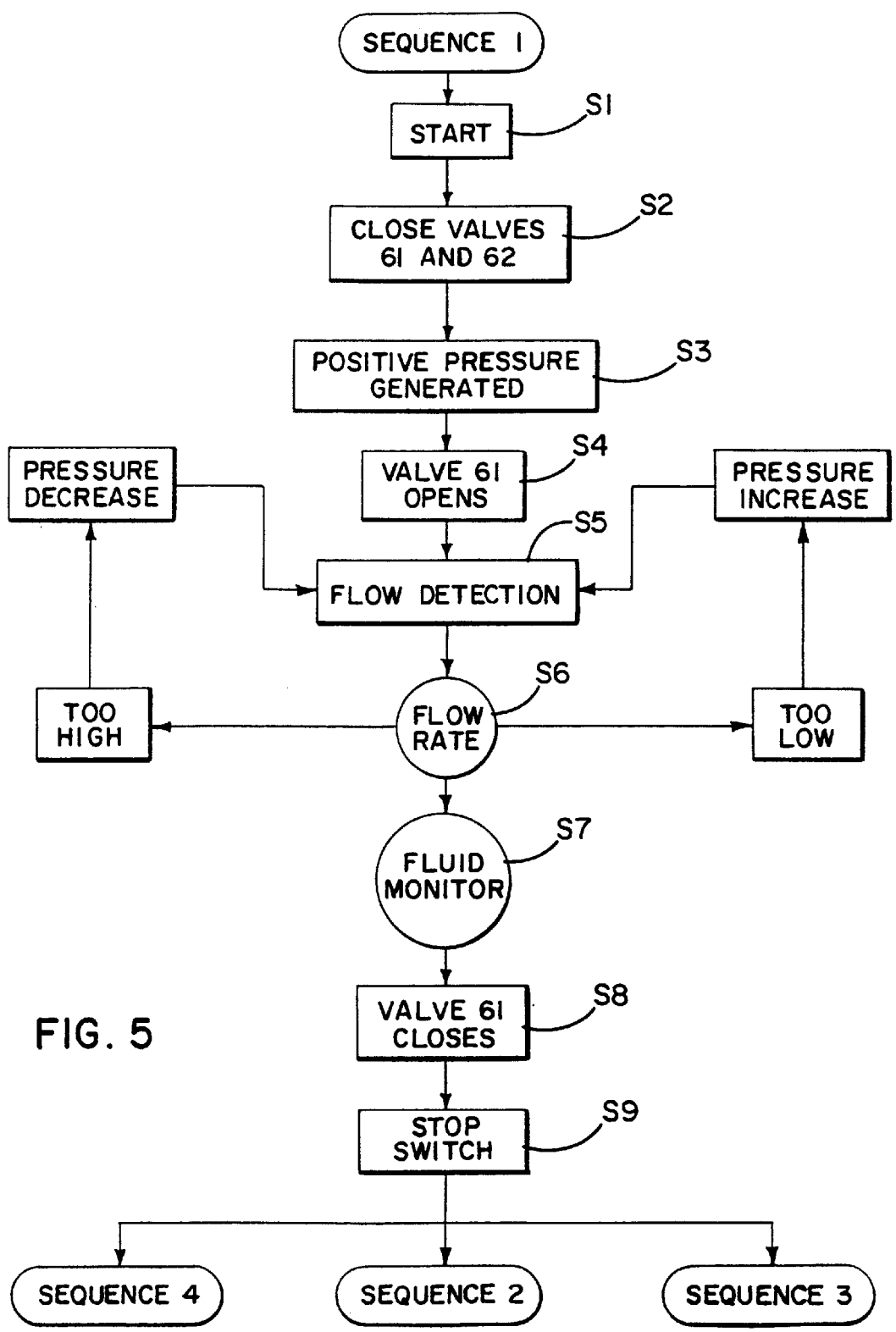
FIG. 5 is a flow chart of an exemplary initial sequence according to the invention.
Figure 6:
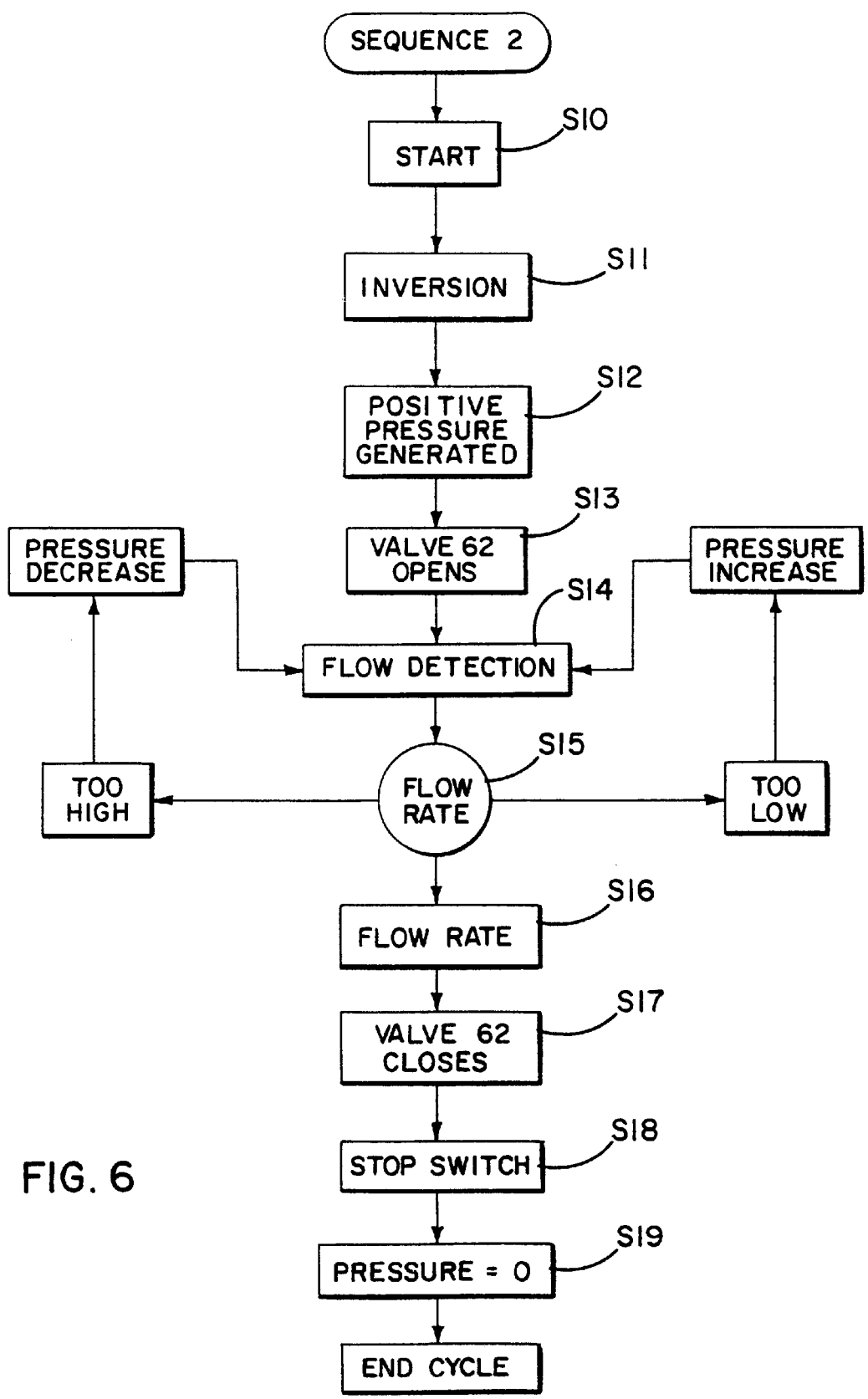
FIG. 6 is a flow chart of an exemplary second sequence according to the invention.
Figure 7:
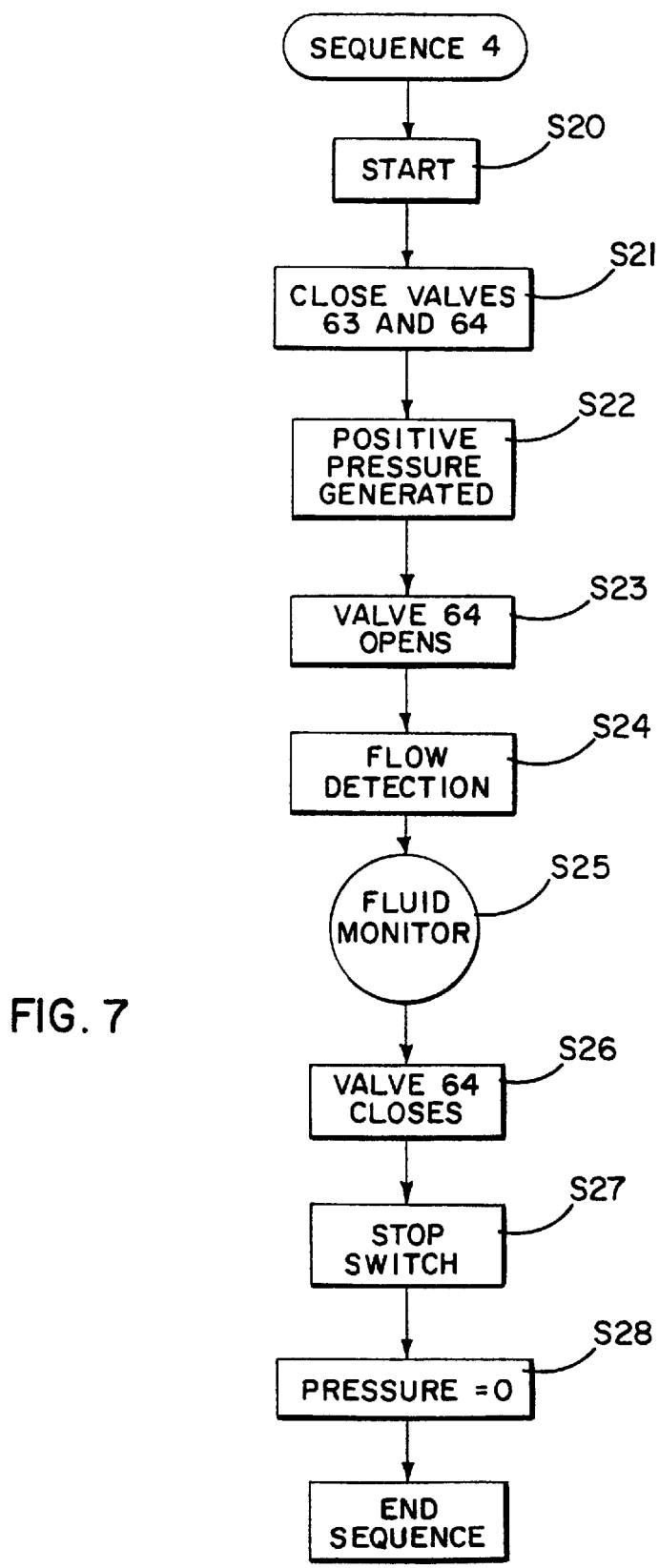
FIG. 7 is a flow chart of an exemplary third sequence according to the invention.
Figure 8:
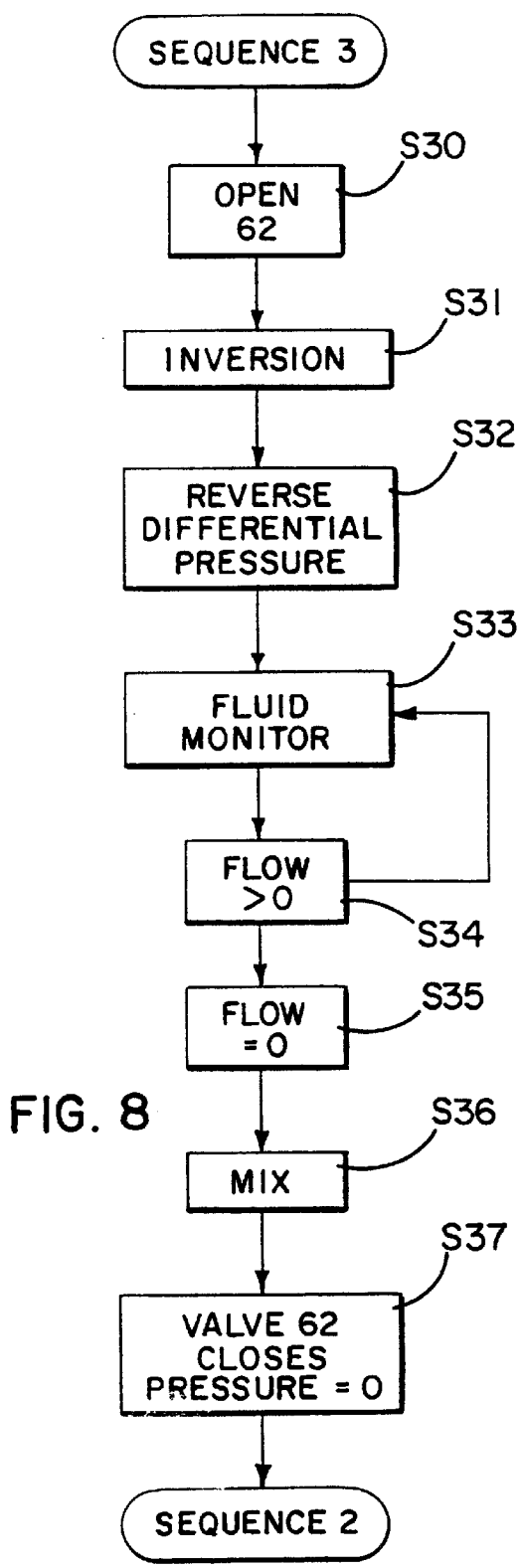
FIG. 8 is a flow chart of an optional priming sequence.

For example, with respect to the embodiments illustrated in FIGS. 1 and 4, a gas inlet 99 or 74 may allow gas into a biological fluid processing system, e.g., to increase the recovery of biological fluid that may otherwise be retained in various components of the system during processing. With respect of FIGS. 1, 3 and 4, a gas outlet 98, 73, or 75 may allow gas that is present in the biological fluid processing system to be separated from the biological fluid being processed, e.g., by separating gas from the system or by displacing gas to another part of the system. In a preferred embodiment of the invention, either or both of the gas inlet and the gas outlet may be selectively operable between an open and closed position by the control arrangement.

In other embodiments, at least one of a gas collection and displacement loop and a gas container (not shown) may be used to move gas, more preferably to separate gas from the biological fluid and/or from the container of biological fluid; or to recover biological fluid retained in various components of the system. For example, biological fluid may be passed through a filter assembly 12, 13 and/or 17, and the fluid passing therethrough, along with the gas displaced by the fluid, may be collected in a satellite container. Gas may be separated by passing it into a gas collection and displacement loop. In some embodiments, the separated gas may be used to purge the conduits and assemblies, e.g., by passing the gas into the inlet of the assembly, thus "chasing" trapped fluid into the downstream container. In another aspect, gas may be sorted or collected in a gas container, and this gas may be fed through at least one of a conduit, a porous medium and a filter assembly, to purge the biological fluid, thereby facilitating the recovery of the biological fluid trapped during processing.

An exemplary gas inlet and gas outlet may be described by reference to FIGS. 3 and 4, both of which illustrate optional flow paths which may be added to a biological fluid processing assembly 10. When such a flow path is inserted into an assembly, it may be desirable to remove gas from the flow path. In FIG. 3, this may be accomplished by activating or opening gas outlet 73. In FIG. 4, gas outlet 75 may be opened or activated to remove air from the flow path, and gas inlet 74 may be opened or activated to allow additional recovery of biological fluid from the filter assembly 17. In a preferred embodiment, both gas outlet 73 and gas outlet 75 are automatic outlets, i.e., contact with biological fluid closes the outlet automatically. Other exemplary gas inlets and gas outlets are also disclosed in International Publication No. WO 91/17809 and U.S. Pat. No. 5,126,054.

The gas inlet and gas outlet are chosen so that the sterility of the system is not compromised. The gas inlet and the gas outlet are particularly suited for use in closed systems, or may be used later, for example, within about 24 hours of a system being opened.

The gas inlet and the gas outlet each comprise at least one porous medium designed to allow gas to pass therethrough. A variety of materials may be used, provided the requisite properties of the particular porous medium are achieved. These include the necessary strength to handle the differential pressures encountered in use and the ability to provide the desired permeability without the application of excessive pressure. In a sterile system, the porous medium should also preferably have a pore rating of about 0.2 micrometer or less to preclude bacteria passage.

To that end, a gas inlet or gas outlet may be included in any of the various elements of the biological fluid processing system. By way of illustration, a gas inlet or gas outlet may be included in at least one of the conduits which connect the different containers, in a wall of the containers that receive the processed biological fluid (i.e., the receiving containers), or in a port on or in one of those containers. The gas inlet or gas outlet may also be included on or in a combination of the elements mentioned above. Also, an assembly or porous medium may include one or more gas inlets or gas outlets. Generally, however, it is preferred to include a gas inlet or gas outlet in the conduits which connect the containers or in a filter assembly. Included within the scope of the invention is the use of more than one gas inlet or gas outlet in any conduit, receiving container, assembly, or porous medium.

It will be apparent to one skilled in the art that the placement of at least one gas control element such as a gas inlet or a gas outlet may be selected to achieve a desired result. For example, it may be desirable to locate the gas inlet upstream of a porous medium and in or as close to the source container of biological fluid as is practical in order to maximize the recovery of biological fluid. Also, it may be desirable to locate the gas outlet downstream of the porous medium and as close to the receiving container as is possible in order to maximize the volume of gas that is removed from the system.

In an embodiment of the invention, air or gas may be stored and/or collected in at least one container such as gas container; upon opening of a flow control device, gas can be fed through them to purge the conduits and assemblies, thereby facilitating the recovery of biological fluid that may have been trapped during processing.

Preferably, the purge air or gas is fed to the conduits at a point as close as is reasonably possible to a source container to maximize the volume of biological fluid recovered. The gas container is preferably flexible so that the gas therein may be fed to the system merely by simple compression.

In accordance with the invention, recovery from the various elements of the biological fluid processing system may be maximized. For example, biological fluid may be processed and expressed to a receiving container through the appropriate conduits and porous media, if any. Biological fluid that has become entrapped in these elements during processing may be recovered either by passing purge gas through the conduits and porous media, or by creating at least a partial vacuum in the system to draw out the retained biological fluid and to permit it to drain into the appropriate receiving container or assembly.

The purge gas may be from any of a number of sources. For example, the biological fluid processing system may be provided with a storage container for the storage of the purge gas, the purge gas may be the gas that was removed from the system or displaced from one part of the system to another part of the system during processing, or the purge gas may be injected aseptically into the system from an outside source (e.g., through a syringe). For example, it may be desirable to use sterile purge gas that has been sterilized in a separate container apart from the biological fluid processing system.

The gases separated by at least one gas control element, e.g., by the gas outlet, may be vented from the system, or they may be collected in a gas container (not shown) and returned to the system as a purge gas to facilitate the recovery of biological fluid that becomes trapped in the various components of the system.

In accordance with an embodiment, a gas collection and displacement loop may be in fluid communication with a selected conduit of the biological fluid processing assembly 10. For example, one end of the loop may be in fluid communication with the upstream end of a filter assembly, e.g., with conduit 25 and the other end of the loop may be in fluid communication with the downstream end of a filter assembly, e.g., with conduit 26. In a preferred embodiment, the gas collection and displacement loop includes at least one flow control device.

In accordance with the invention, the gas collection and displacement loop provides a flow path for separating gas from the biological fluid flow path, and, optionally, using that collected gas to recover additional biological fluid. The loop may also include a container such as a gas container interposed in the loop for collecting and storing the displaced gas, and for collecting and isolating processed (e.g., leukocyte depleted) biological fluid. For example, leukocyte depleted biological fluid may be collected in a gas collection and displacement loop for sampling. In a more preferred embodiment, the container may be a flexible bag which can be squeezed in order to transfer gas. Included within the scope of the present invention are other structures which function as described above, such as a syringe, or the like, which could draw gas from the processing assembly into the loop, and could transfer the collected gas in the syringe into another container and/or conduit. It is intended that the gas collection and displacement loop function so that leukocyte-laden fluid is isolated from the leukocyte depleted fluid.

In an alternative embodiment, the gas collection and displacement loop may include a liquid barrier medium through which gas passes. The liquid barrier medium may be any of a variety of means and devices which are capable of separating gas that may be present in the blood processing system from the biological fluid that is processed in the system. The liquid barrier medium may be included in a housing to form a liquid barrier assembly. Suitable liquid barrier media and barrier assemblies include those disclosed in International Publication No. WO 91/17809. In a more preferred embodiment, the gas collection loop includes at least one conduit, a gas collection container, preferably a flexible gas container, and a liquid barrier medium upstream of the gas container. In this embodiment, processed biological fluid (e.g., leukocyte depleted biological fluid passing through a filter assembly) may be collected in a satellite bag, and gas in the satellite bag may be displaced through the gas collection and displacement loop into the gas collection container. If desired, processed biological fluid may also be displaced from the satellite bag into the gas collection container. In this embodiment, contaminated (leukocyte-containing) biological fluid is unable to pass through the liquid barrier medium, thus isolating contaminated biological fluid from the non-contaminated biological fluid.

A number of additional containers may be in communication with the biological fluid processing system, and can be utilized to define different flow paths. For example, an additional satellite bag containing physiological solution may be placed in communication wit the biological fluid processing system upstream of the leukocyte depletion assembly, or downstream of the leukocyte depletion assembly and the solution may be passed through the leukocyte depletion assembly so that the biological fluid that was held up in the assembly can be collected.

It will be appreciated that when the biological fluid from the collection bag 11 is expressed toward one or more satellite bags, some of the biological fluid may be trapped in the conduits and/or a porous medium.

In accordance with the invention, an automated control arrangement 50, in response to predetermined conditions, sends and receives signals, and controls the overall sequence and flow of biological fluid from a first container such as the collection container 11 to any of the receiving or satellite containers. For example, the automated control arrangement may include one or more devices, switches, and/or indicators, sensors or monitors to achieve a desired purpose, including, but not limited to: a power switch; a start switch; a stop switch; a sequence selection switch; weight sensor devices, switches, and/or indicators; time sensor devices, switches, and/or indicators; optical sensor devices, switches, and/or indicators; and fluid flow sensor devices, switches, and/or indicators temperature devices, switches and/or indicators; and at least one interface monitor for sensing the point of separation between the first portion or component of the biological fluid and a second portion or component. As used herein, monitoring the interface includes a monitor associated with a porous medium such as a red cell barrier medium, for monitoring the flow rate of the first portion or the back pressure upstream of the porous medium such as a red cell barrier medium; an optical sensing device, for monitoring the transition between the first and second portions of the biological fluid; a weight sensing device or a total flow monitor, for sensing a predetermined weight or amount of biological fluid which defines the separation point between the first and second portions or components of the biological fluid; and any other mechanism for sensing the separation of one portion or component of the biological fluid form another portion or component.

It is intended that each of these sensors monitor a predetermined condition, and react or provide feedback according to a predetermined or pre-set array of variables. Accordingly, any step and/or sequence (e.g., including two or more steps) for processing a biological fluid may be carried out according to the invention. Thus, the biological fluid may typically separated into fractions, components and/or constituents; passed from one location to another, which may include isolation of a portion of the biological fluid for sampling, passage through at least one porous medium, passage across at least one separation medium, combining or pooling the biological fluid, administering a biological fluid to a patient, and/or chasing the biological fluid with gas. The biological fluid may, for example, be heated, cooled, diluted, fractionated, lyophilized, washed, exposed to a viricidal agent, and/or any combination of the above. At least one fluid including, but not limited to an additive, anticoagulant, preservative, viricidal agent, and a gas may be added to the biological fluid or separated from the biological fluid.

For example, in one sequence, involving directing biological fluid tangentially from a source container to a separation medium such that plasma passed through the separation medium to a satellite container, and red cells and/or platelets pass across the separation medium to the source container and back, to the separation medium, a weight sensor receiving a signal from at least one of the containers may trigger a predetermined command in the automated control arrangement which stops the sequence.

In an embodiment according to the invention involving passing biological fluid through a porous medium such as a red cell barrier medium or a red cell barrier/leukocyte depletion medium, as flow through the medium slows or stops, a flow sensor may trigger a predetermined command in the automated control arrangement which stops sequence 1 and initiates sequence 2 and/or sequence 3 as shown in the figures.

The automated control arrangement 50 may be connected to the various elements of the system, and may include one or more connections to the biological fluid processing assembly, including a container, or a flow control device, a gas control element, a conduit, to a specific element in the biological fluid processing assembly or the pressure differential generator.

The operation of an automated biological fluid processing system in accordance with one aspect of the invention may be illustrated by reference to the automated processing system shown in FIG. 1 and the flow charts shown in FIGS. 5–11.

In step 1 (hereinafter, S1, S2, S3, etc.), Sequence 1 is started. The initial sequence may include collecting the biological fluid directly into the collection bag 11, selecting the first sequence selection, placing the collection container 11 in differential pressure generator 51, and connecting the collection container to any satellite containers, if necessary. In a preferred embodiment of the invention, the collection container 11 contains a biological fluid, typically whole blood, which has been separated into a supernatant layer 31 and a sediment layer 32 before placing the collection container 11 in the differential pressure generator and selecting the first sequence. If whole blood is used, the supernatant layer may be primarily PRP, and the sediment layer may be primarily PRC. In an embodiment of the invention, the biological fluid can be separated under conditions in which a transition layer or intermediate layer (typically buffy coat) spans the interface between the supernatant layer and the sediment layer. In another embodiment of the invention, the supernatant layer may be primarily PPP and the sediment layer maybe primarily red cells with an intermediate layer of buffy coat between them. The biological fluid may be expressed from the collection bag as separate supernatant, intermediate, and sediment layers, respectively. These layers can be expressed in any order.

In S2, valves 61 and 62 are closed. Alternatively, the valves may be closed in the first step in the initialization of the sequence. In S3, a differential pressure may be generated between collection container 11 and satellite bag 41.

In S4, valve or clamp 61 is opened, and the pressure differential between the collection container and first satellite bag 41 causes the supernatant layer to flow in the direction of satellite bag 41. As the supernatant layer passes from the collection bag to the first satellite bag, it may pass through at least one porous medium such a leukocyte-depletion medium, a red cell barrier medium, or a combined leukocyte depletion red cell barrier medium. In another embodiment (not shown), the supernatant fluid maybe passed through a separation assembly S1, interposed between a container such as collection container 11 and a container such as a satellite container 41.

In S5 and S6, the initial flow rate of the supernatant is monitored. If the flow rate is too high or too low, a signal may be generated whereby the differential pressure is decreased or increased. Alternatively, if the flow rate is typically stable at a constant pressure, adjusting the pressure may be unnecessary.

After a suitable initial flow is achieved in S6, the flow continues to be monitored in S7 until a predetermined value is reached, at which point, a signal is produced to indicate that flow should cease. In accordance with the invention, the nature of the signal will depend upon the type of monitor used to distinguish one layer of biological fluid from another. For example, in a preferred embodiment of the invention, a red cell barrier or a combined leukocyte depletion red cell barrier porous medium is used, and the monitor produces a signal when the flow rate significantly slows, for example stops. In an embodiment of the invention which includes a weighing device, the monitor may produce a signal when a predetermined amount of supernatant layers has passed into the satellite bag 41. In an embodiment of the invention which includes a optical reader, the monitor may produce a signal when the fluid passing the optical reader reaches a predetermined density. It is intended that the invention should not be limited by the type of flow detection and monitoring system employed.

In S8, the signal produced in S6 and S7 closes valve or clamp 61 is closed in response to the signal which indicates flow should cease. In S9, the process may be stopped completely, or one or more additional sequences, such as Sequence 2, 3 or 4, may be selected manually or automatically.

In Sequence 1, the supernatant layer was the first layer to be expressed from the collection bag. In alternative embodiments, the initial sequence may include first expressing a layer other than the supernatant layer. For example, the red cell sediment layer or buffy coat may be expressed first.

If Sequence 2 is selected, the process typically the processing of the sediment layer, is started in S10.

In accordance with the invention, it may be desirable to remove gas or air from the system or to separate or move gas/air from one part of the system to another part. In accordance with the present invention, any arrangement or method which affects removal or displacement of gas/air in the system may be used.

In accordance with the invention, it may be desirable to mix the contents of a container such as a collection bag and/or a satellite bag, e.g., to mix a biological fluid with an additive solution or the like, and/or to mix blood components.

In an embodiment of the invention, the process may include S11 in which the collection container is inverted or rocked, either by rotating the collection bag within the pressure differential generator, or by rotating the pressure differential generator itself. Inversion of the bag and/or pressure differential generator may be a desirable process step to achieve a variety of result, including but not limited to displacing gas within the collection bag and mixing a biological fluid with an additive solution, diluent, or the like, to orient the bag in a desired position, or to invert a bag which contains air. At the completion of the inversion step, conduit 62 may be oriented in a desired position, typically approximately 180° from its position at the beginning of S11.

In S12, a positive pressure is generated, valve 62 is opened (S13), and sediment layer 32 in collection bag 11 may be passed through a leukocyte depletion assembly 17 and into a container, such as the second satellite bag 18. S14 and S15 may correspond to S5 and S6, respectively, to assure that the desired initial flow rate is maintained. After a suitable initial flow is achieved, the flow continues to be monitored in S16. When the flow rate slows or stops (S16), preferably when substantially all of the sediment layer has been expressed from the collection bag, valve 62 is closed (S17), a stop switch may be activated (S18), and the pressure differential is preferably reduced to zero (S19).

If sequence 3 is selected to follow sequence 1, an anticoagulant solution or an additive solution or the like in second satellite bag 18 may be passed from the second satellite bag 18 into collection container 11. In S30, valve 62 is opened by the control unit 50. In S31, the collection container 11 is inverted either by rotating the collection bag within the pressure differential generator, or by rotating the pressure differential generator. The sediment layer 32 then moves to the end of the collection container 11 which communicates with the conduit 25 while any air moves to the opposite end of the collection container 11. In S32, a reverse or negative pressure is generated between the collection container 11 and the second satellite bag 18, drawing the solution in the second satellite bag 18 into the collection container 11. Alternatively, the negative pressure differential may be generated first and the valve 62 may then be opened, or the second satellite bag 18 may be contained in another pressure differential generator 51B which forces the additive into the collection bag 11. In S33–S35, the flow is monitored until the flow falls to a value, such as zero, which indicates a sufficient amount of the solution has been drawn into the collection container 11. In S36, mixing of the solution and the sediment layer 12 is initiated. The solution and the sediment layer 32 may be mixed in a variety of ways, for example, by rotating or rocking the collection container 11 and/or the differential pressure generator 51 or by providing a mechanism in the differential pressure generator 51 which manipulates the collection container 11. After valve 62 is closed (S45), the pressure in the differential generator 52 is reduced to zero and sequence two may be initiated as described above.

Sequences 1, 2 and 3 can thus be implemented in the automated fluid processing system shown in FIG. 1. With the physiologically acceptable solution initially stored in the second satellite bag 18, the control unit 50 may step first through Sequence 1 to express the supernatant layer in the collection bag 11 into the first satellite bag 41, then though Sequence 3 including steps S30 and S37 to add the solution in the second satellite bag 18 to the sediment layer in the collection bag 11, and then through Sequence 2 except for the inversion step S11 to express the sediment layer in the collection bag 11 into the second satellite bag 18. The inversion step S11 in Sequence 2 is unnecessary because the collection container 11 has already been inverted in S31 of Sequence 3.

As noted in S9 above, the supernatant layer may be subjected to additional processing, if desired, preferably downstream of the porous medium 12 and/or 13, either connected to the system or after being separated from the system. For example, when a desired amount of the supernatant fluid has been collected in first satellite bag 41 it may be passed from satellite bag 41 to a separation medium, e.g., to separate the plasma from the platelets. Alternatively, the supernatant fluid may be separated into a second supernatant layer, and a second sediment layer. Typically, if the supernatant fluid is PRP, it may be separated into a second supernatant layer including plasma and a second sediment layer including platelets, which may be processed to form PC.

For example, if Sequence 4 is selected after Sequence 1, the automated processing system may be used to separate plasma from platelets. In S21, valves or clamps 63 and 64 are closed. Alternatively, the valves may be closed as the first step in the initialization of Sequence 3. In step 22, a positive pressure differential is generated between satellite bag 41 and satellite bag 42. The differential pressure may be generated by substituting the second satellite bag 41 for the collection bag 11 in the differential pressure transducer 51 or by providing another differential pressure transducer 51B for the second satellite bag 41. Once a desired pressure is reached, valve 64 may be opened (S23), allowing the second supernatant layer to flow through conduit 28 into satellite bag 42.

In S24 and S25, flow continues until a predetermined value or condition is reached, e.g., a sufficient amount of second supernatant layer has passed into satellite bag 42. In accordance with the invention, the amount of supernatant layer passing into satellite bag 41 may be predetermined, e.g., based on time, weight or density, but it is intended that the invention should not be limited thereby.

In S26, after the predetermined amount of second supernatant layer has been collected, valve 64 closes, a stop switch may be activated (S27), and the pressure differential may be reduced to zero (S28).

Figure 2:
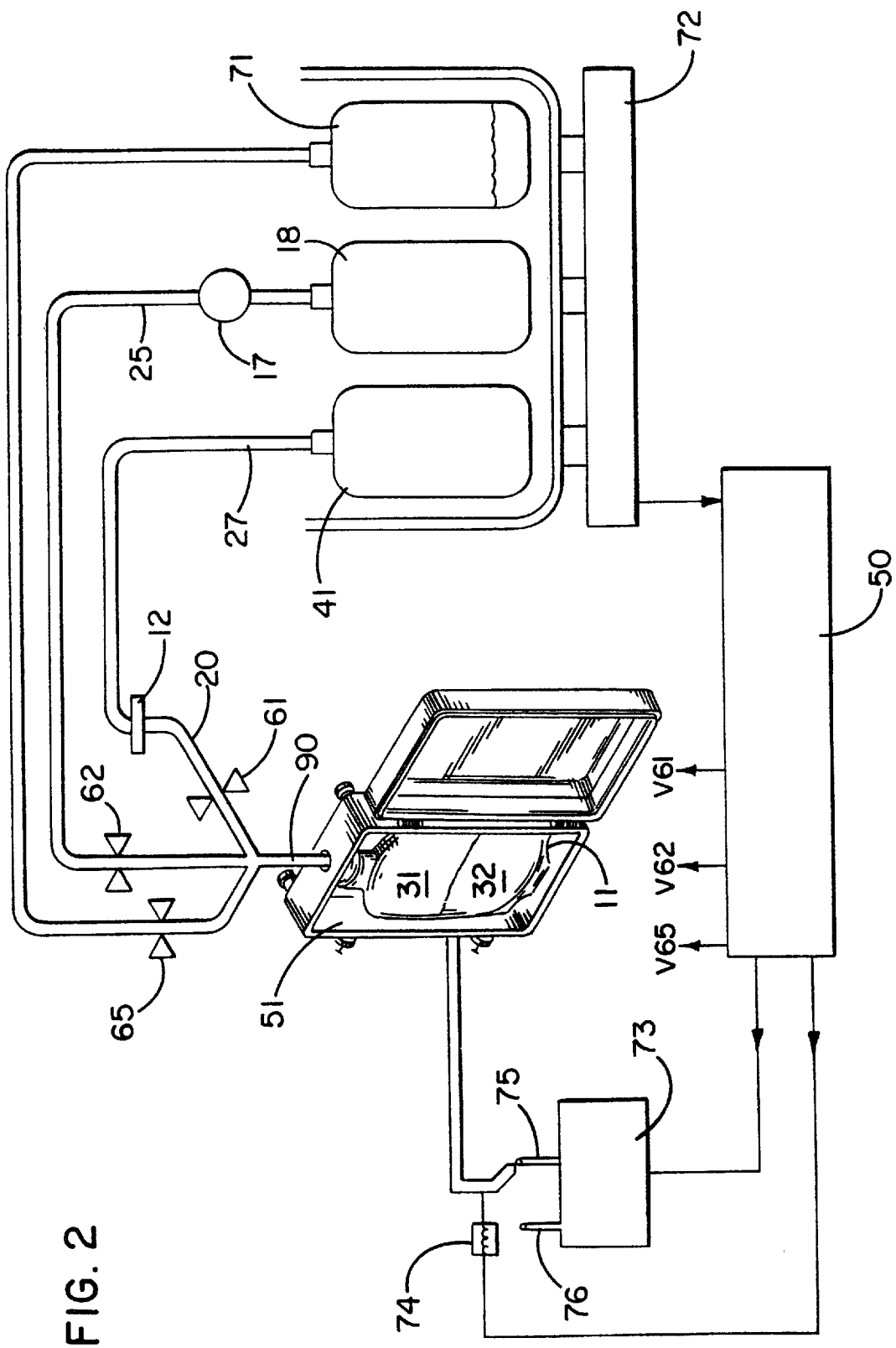
FIG. 2 is another embodiment of a biological fluid processing system according to the invention.
Figure 9:
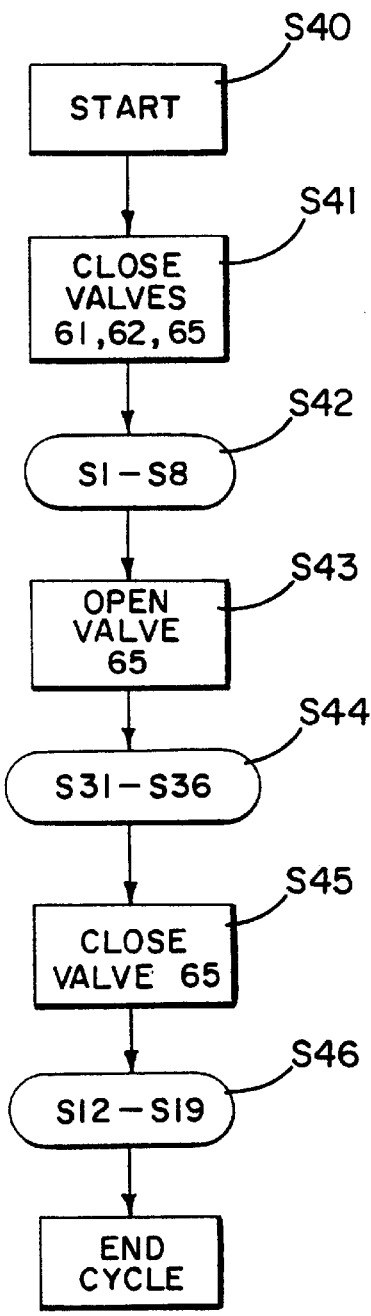
FIG. 9 is a flow chart of an exemplary sequence according to the invention.

The operation of the automated biological fluid processing system in accordance with another aspect of the present invention may be illustrated by reference to the automated processing system shown in FIG. 2 and the flow chart shown in FIG. 9. In this exemplary embodiment, collection container 11, which includes biological fluid which has been separated into a supernatant layer 31 and a sediment layer 32, may be positioned in a differential pressure generator 51. In this exemplary embodiment, it is preferred that the differential pressure generator 51 is a combined pressure and vacuum expressor. Collection container 11 may be in fluid communication with a first satellite bag 41 suitable for receiving the supernatant layer 31, a second satellite bag 18 suitable for receiving a sediment layer 32, and a fourth satellite bag 71 suitable for storing physiologically acceptable solution, such as a nutrient solution of a preservative solution. The fluid flow path between the collection container 11 and the first satellite bag 41 preferably includes a red cell barrier porous medium or a combined leukocyte depletion red cell barrier porous medium and the fluid flow path between the collection container 11 and the second satellite bag 18 preferably includes a leukocyte depletion porous medium.

The three satellite bags may be positioned in or on a flow monitor 72 suitable for monitoring flow by weighing the amount of fluid in the respective satellite bags. Flow monitor 72 maybe connected to control unit 50, preferably a microprocessor controller. Control unit 50 may be connected to the pressure differential generator 51 through pump 73 and valve 74, preferably a two-way valve, suitable for inducing pressure or a vacuum on collection container 11. In a preferred embodiment, pump 73 can create positive pressure on collection bag 11 through line 75 and can create a reverse or negative pressure, i.e., a vacuum in collection bag 11 through line 76.

As this sequence is initiated, the flow paths leading from the collection bag 11 to all of the satellite bags are closed (S41). In S42, steps S1 through S8 of Sequence 1 may be conducted, whereby a differential pressure between collection bag 11 and satellite bag 41 is established and the supernatant layer is expressed into satellite bag 41. Valve 61 may then be closed (S8) and valve 65 opened (S43).

In S44, steps S31 through S36 of Sequence 3 are conducted, whereby an anti-coagulant solution or an additive solution or the like in fourth satellite bag 72 is passed form fourth satellite bag 71 into collection container 11. In S31 the collection container 11 is inverted, e.g., as described with respect to S11. The sediment layer 32 then moves to the end of the collection container 11 which communicates with the conduit 90 while any air moves to the opposite end of the collection container 11. In S32, a reverse or negative pressure is generated between the collection container 11 and the fourth satellite bag 71, drawing the solution in the fourth satellite bag 71 into the collection container 11. Alternatively, the negative pressure differential pressure may be generated first and the valve 65 may then be opened. In S33–35, solution flow is monitored until it falls to a value, such as zero, which indicates a sufficient amount of the solution has been drawn into the collection container 11. Mixing of the solution and the sediment layer 32 is then initiated in S36. The solution and the sediment layer 32 may be mixed in a variety of ways, for example, by rotating or rocking the collection container 11 and/or the differential pressure generator 51 or by providing a mechanism in the differential pressure generator 51 which manipulates the collection container 11. After valve 65 is closed (S45), sediment layer 32 may then be expressed into second satellite bag 18 (S46) by following steps S12 through S19 of Sequence 2.

In accordance with an additional embodiment of the invention, a method is provided whereby the recovery of various biological fluids trapped or retained in various elements of the system is maximized, either by causing a volume of gas behind the trapped or retained biological fluid to push the fluid through those elements and into the designated container, or by drawing the trapped or retained fluid into the designated container, by pressure differential (e.g., gravity head, pressure cuff, suction, and the like). This provides for a more complete emptying of the container, assembly, or porous medium. Once the container, assembly or porous medium is emptied completely, the flow may be stopped automatically.

Figure 10:
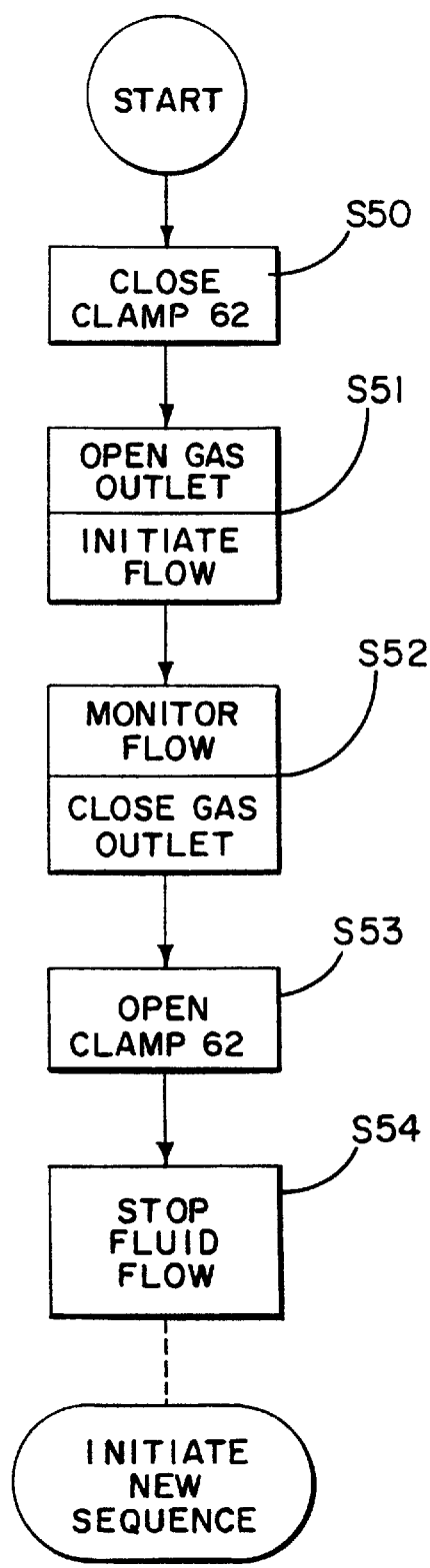
FIG. 10 is a flow chart of an optional venting sequence according to the invention.

FIG. 10 includes an exemplary flow chart for an embodiment of the invention which includes separating gas in the system from the biological fluid to be processed. In a preferred embodiment, gas in the system may be displaced to a part of the system separate from the biological fluid; in a more preferred embodiment, gas in the system may be expelled from the system.

In an exemplary embodiment, in which a gas outlet and additive/priming solution is used to prime a leukocyte depletion filter assembly 17, a gas outlet 98 and a gas inlet 99 may be positioned as shown in FIG. 1 and container 18 includes an additive/priming solution. In S50, clamp 62 is closed. In S51, gas outlet 98 is activated or opened, and a differential pressure is generated between container 18 and the ambient environment of the gas outlet 98 so that a column of additive solution flows through conduit 26, through leukocyte depletion filter assembly 17, and into conduit 25. In some embodiments, the pressure differential may be generated by gravity head, and container 18 may be inverted. In the illustrated embodiment, the pressure differential is generated by pressure differential generator 51A. As the solution advances, it pushed gas in the conduit ahead of it until the gas reaches gas outlet 98. Gas ahead of the column of additive solution passes through the outlet and out of the system.

In S52, before the solution reaches a predetermined position upstream of the gas outlet, the column of additive solution triggers a monitor which closes a valve in the fluid flow path leading to the gas outlet or depressurizes the pressure differential generator 51B, if the gas outlet is a non-automatic gas outlet. Optionally, if the gas outlet is an automatic outlet, no monitor is required, or a monitor may signal the location of the additive solution. In S53, clamp 62 opens , and additive solution flows into container 11. In S54 the flow of additive/priming solution is stopped or completed. The flow path between container 11 and container 18 is now prepared for use in accordance with the invention, for example, by the initiation of Sequence 2.

After passing a biological fluid through the system, for example, in Sequence 2, ambient air or a sterile gas may enter the system through gas inlet 99 in order to recover the biological fluid retained in the system. If gas inlet 99 is a manual inlet, the inlet is opened and/or a clamp is released; if the gas inlet 99 is automatic, the pressure differential between the gas inlet and satellite bag 18 will cause the gas to flow through conduit 25, through leukocyte filter assembly 17, and toward satellite bag 18. In some embodiments the container 18 and the leukocyte 17 may be positioned at a point below that of container 11, preferably with container 18 in an upright position, before activating gas inlet 99. In the process, retained biological fluid that is trapped in those elements during processing are recovered from those elements and collected in satellite bag 18.

Figure 11:
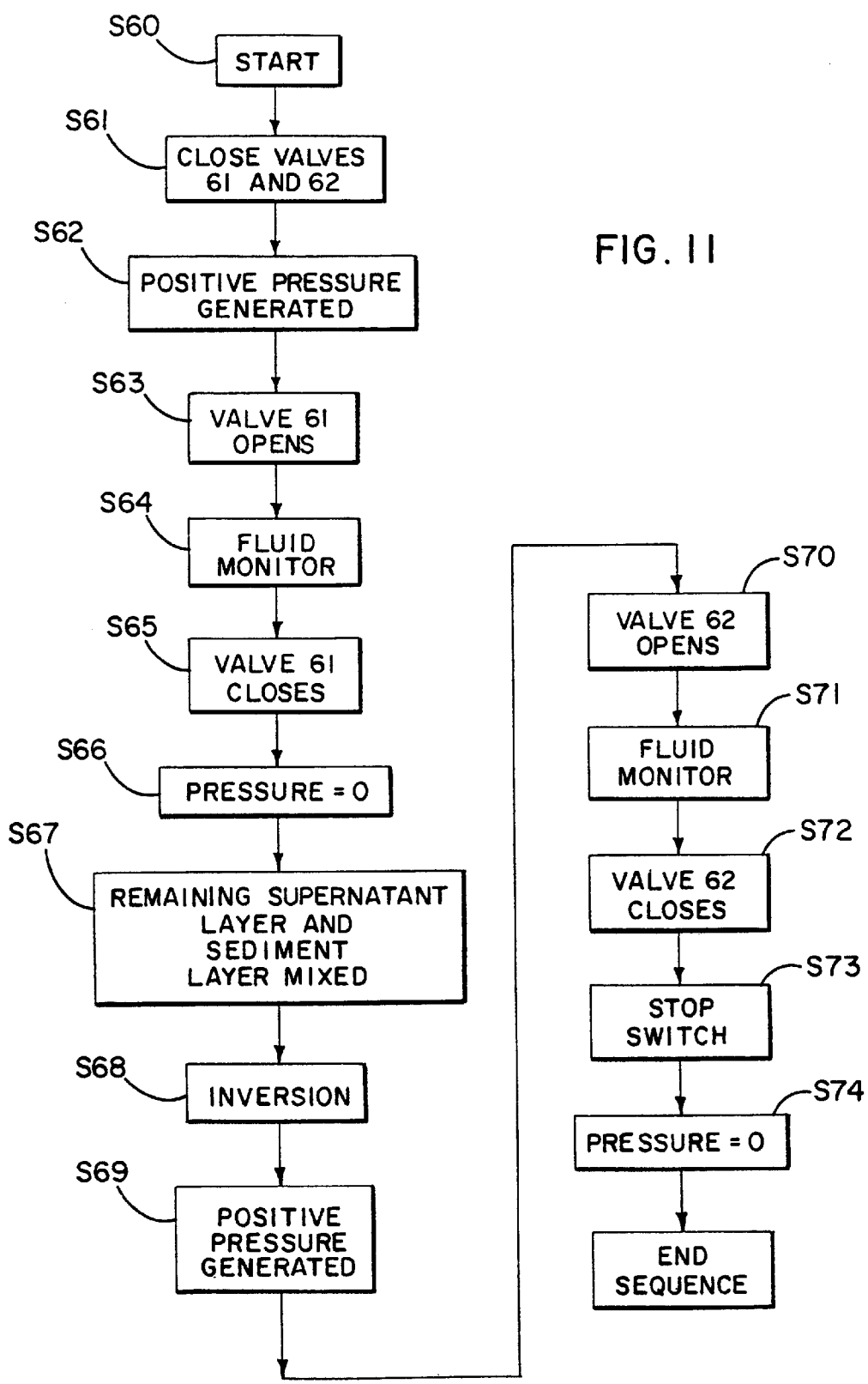
FIG. 11 is a flow chart of an exemplary sequence according to the invention.

FIG. 11 illustrates another exemplary flow chart for an embodiment of the invention as shown in FIG. 1. Initially a collection bag 11 containing a supernatant layer 31 and sediment layer 32 is placed in the differential pressure generator 51. The system is then started and allowed to stabilize is S60 and the valves 61 and 62 are closed in S61. Alternatively, the valves 61 and 62 maybe closed before the system is started.

A positive pressure is generated in S62 and valve 61 is opened in S63 and flow begins. The flow of the supernatant layer is monitored in S64, to express an amount of the supernatant layer which is less than the total amount of the supernatant layer. For example, the fluid monitor may monitor the weight of collection bag 11 and/or satellite bag 41. Alternatively, the flow rate over time may be monitored. After a predetermined amount of the supernatant layer has been expressed, valve 61 is closed in S65, leaving a desired amount of supernatant layer 31 with the sediment layer 32 in the collection bag 11.

The desired amount of supernatant fluid from supernatant layer 31 to be left in collection bag 11 will vary depending on the intended use of the remaining contents of the bag, e.g., the sediment layer 32 and/or the intermediate layer between the supernatant and sediment layers.

For example, if the sediment layer is PRC, and the supernatant layer is PRP, and the PRC is intended to be used for transfusion, a sufficient amount of PRP may be left in the collection bag 11 to produce a hematocrit of about 52% or greater, more preferably a hematocrit of about 70% to about 80%, or more.

Alternatively, if the supernatant layer is PPP, with an intermediate layer of buffy coat between the PPP and the sediment layer of PRC, an amount of PPP maybe left in the collection bag 11 to be processed with the buffy coat.

After valve 61 is closed in S65, the positive pressure is decreased to 0 in S66. Optionally, the contents of the collection bag 11, i.e., the remaining supernatant layer and the sediment layer, may be mixed in S67. Suitable techniques for mixing include those as described in Sequence 4. The collection bag 11 may be inverted and/or kneaded during mixing, and may be left in the inverted position at the end of the mixing step in S68. A positive pressure is generated in S69, and then valve 62 opens in S70, expressing the remaining fluid from the collection bag 11 to the second satellite bag 18. The flow of the fluid from the collection bag is monitored in S71 to determine when flow ceases.

Valve 62 then closes in S72. The pump is shut off in S73, and the pressure reaches zero in S74, thus completing the sequence.

In other embodiments, e.g., involving the buffy coat, other sequences may be utilized. For example, buffy coat may be isolated by any known technique, including separating whole blood into a supernatant layer of PPP, an intermediate buffy coat layer, and a sediment layer of PRC and separating the layers as noted above. After the unit of buffy coat is separated, it maybe pooled with other units of buffy coat. Pooled or unpooled buffy coat may be separated, typically by centrifugation, to form a supernatant platelet containing layer and a sediment red cell containing layer in a satellite bag.

The satellite bag (which is connected to an additional empty satellite bag) may be placed in the pressure differential generator, and the empty satellite bag may be placed in or on the flow meter. The supernatant layer may be separated from the sediment layer as described in the sequences above. For example, the supernatant platelet containing layer may be passed through a red cell barrier medium or a combined red cell barrier leukocyte depletion barrier until the flow rate nears or reaches zero.

A preferred Differential Pressure Generator

Conventional expressor have many drawbacks. For example, they apply an uneven pressure to the fluid collection bag and may create wrinkles and folds in the bags. Biological fluids can become trapped in these wrinkles and folds, preventing 100% of the biological fluid form being expressed. Uneven pressure also tends to agitate the fluid within the container, and may, for example, disturb the interface between components, for example, between the supernatant layer and the sediment layer, e.g., the buffy coat, and thus reduce the amount of supernatant layer which can be reliably collected. Additionally, because the collection bag may be distorted and because the structure of convention expressors can hinder observation of the container, it may be difficult for an operator to determine correct operation of the apparatus by watching an interface layer between a sediment and a supernatant layer. Further, in some applications, it is desirable to draw fluid into a container. However, conventional expressors are merely capable of squeezing a container. So while they can force fluid out of the container, they are unable to draw fluid into the container.

Embodiments of the present invention overcome these disadvantages. In accordance with the present invention, an expressor for varying the amount of fluid in a variable-volume container connected to at least one conduit may comprise a housing defining an enclosed chamber for accommodating the container, the housing having at least one opening through which the conduit can extend; a pressure regulating mechanism coupled to the housing to vary the pressure of fluid in the chamber and thereby vary the volume of the container; and an arrangement for moving fluid within the container, the arrangement including at least one of a) a drive mechanism for moving the housing and b) apparatus for pressing against a first portion of the container.

A method for expressing a biological fluid from a container in an enclosed chamber may comprise varying the pressure within the chamber; and moving fluid within the container by at least one of a) moving the chamber is an oscillatory fashion or b) pressing against a first portion of the container.

Figure 12:
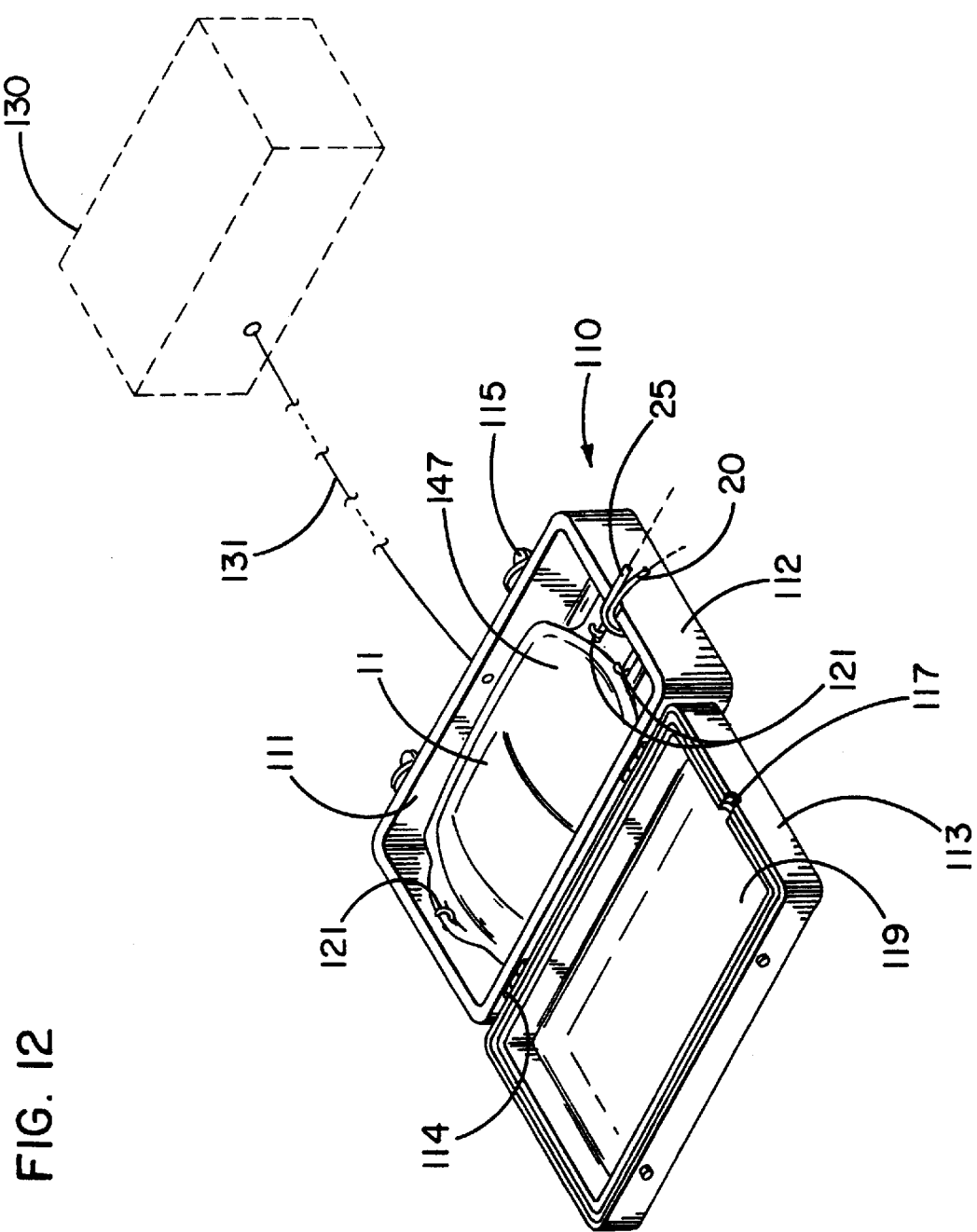
FIG. 12 is a perspective view of a first embodiment of a differential pressure generator for use with embodiments of a biological fluid processing system according to the invention.

As shown in FIG. 12, a first exemplary expressor for use in the present invention comprises a housing 110 which defines an enclosed chamber 111 and a pressure regulating mechanism 130 pneumatically coupled to the housing 110 by a flexible hose 131 or other conduit to vary the pressure within the chamber 111. A variable volume fluid container, such as the collection bag 11 containing a biological fluid, may be placed in the chamber 111 with one or more sections of flexible tubing 20, 25 extending from the collection bag 11 through an opening 117 in the housing 110 to the exterior of the housing 110. The collection bag 11 need not be flexible, but it preferably is constructed so that its internal volume can be varied by controlling the fluid pressure applied to the outside surface of the collection bag 11. The pressure regulating mechanism 130 supplies and/or withdraws a fluid (i.e., either a gas or a liquid) to and/or from the chamber 111 in order to vary the pressure exerted on the collection bag 11 within the chamber 111. This, in turn, varies the volume of the collection bag 11 and thereby forces fluid (i.e., either a liquid or a gas) out of or into the collection bag 11 through the flexible tubing 20, 25.

Figure 18:
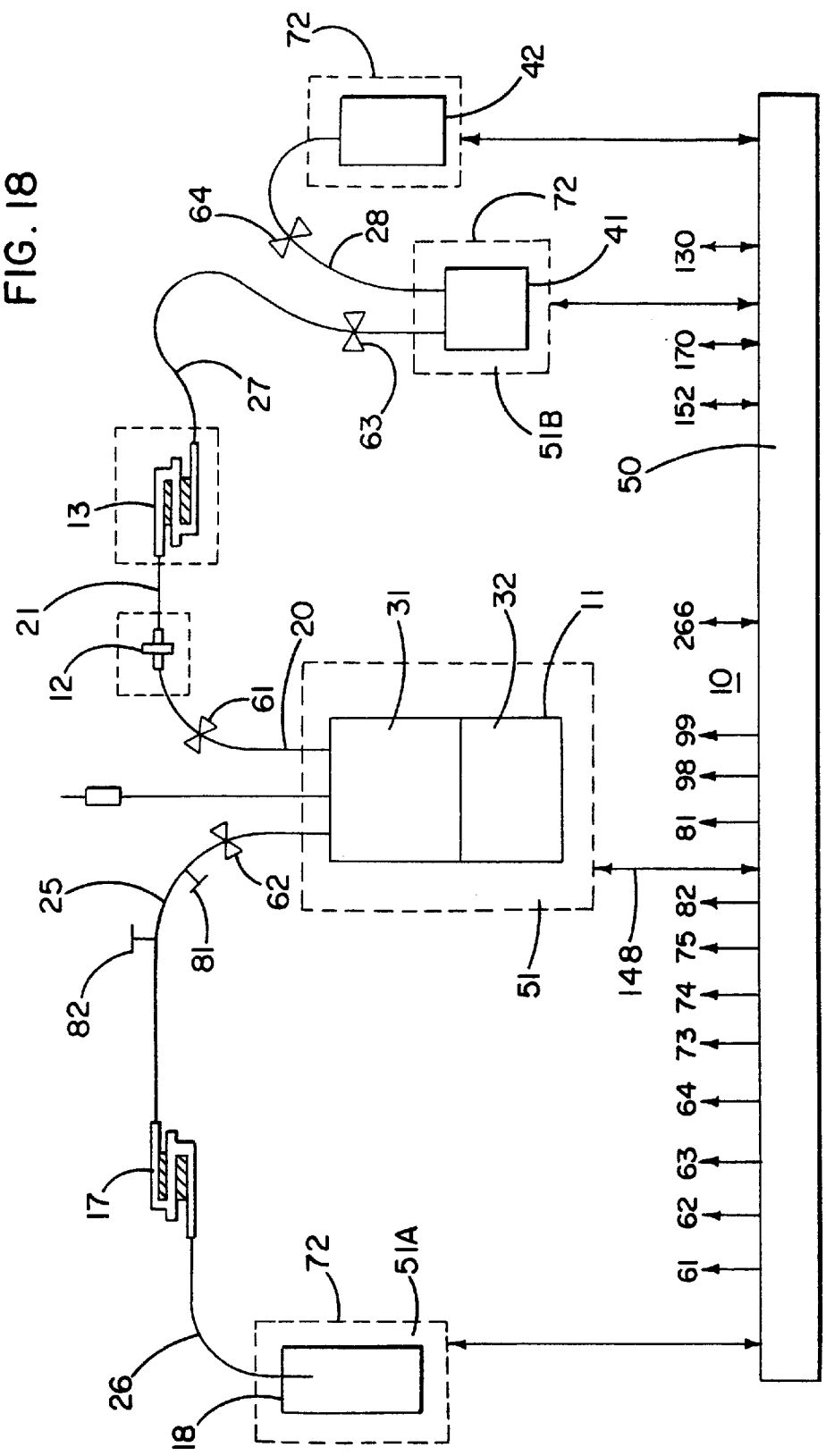
FIG. 18 is a representation block diagram of an embodiment of the biological fluid processing system according to the invention.

Preferably, the pressure regulating mechanism 130 includes a valve arrangement such as a four way pneumatic valve capable of connecting flexible hose 131 to the input or to the output of a standard piston pump. The four-way pneumatic valve is electronically controlled by the control unit 50 (FIG. 18). Additionally, there may be a plurality of relief valves and a pressure sensor electronically controlled and monitored by the control unit 50. In this manner, the control unit 50 may control and monitor the pressure or vacuum exerted on the collection bag 11. The four-way pneumatic valve, the plurality of relief valves, and the pressure sensor may be, for example, disposed in the control unit 50, the pressure regulating mechanism 130, and/or the housing 110.

The housing 110 may be formed from any suitable material which has sufficient structural integrity to withstand the differences in pressure between the chamber 111 and the exterior of the housing 110. The housing 110 may have a variety of configuration. For example, in the expressor shown in FIG. 12, the housing 110 comprises a base 112 and a cover 113 which may be releasably mounted to the base 112 in any suitable manner to form the chamber 111 and envelop the collection bag 11. In the exemplary expressor, the cover 113 is releasably mounted to the base 112 by means of hinges 114 on one side of the base 112 and cover 113 and at least one and preferably two latches 115 on the other side.

The housing also preferably includes a transparent portion positioned to permit observation of the fluid container. For example, the transparent portion may be a window 119 in the cover 113. Alternatively, the entire housing by be formed from a transparent material such as a transparent plastic.

One or more hooks 121 may be mounted inside the chamber 11 at the same end as the flexible tubing 20, 25 and/or at the end opposite from the flexible tubing 20, 25. It was found that utilizing a single hook on the end of the collection bag 11 opposite to the flexible tubing 20, 25 and using one and preferable two hooks on the end of the collection bag nearest the flexible tubing 20, 25 better secured the collection bag 11 within the housing and facilitated expression of fluid from the collection bag 11. Further, if the housing 110 is inverted so that the end opposite the flexible tubing 20, 25 is facing up, the collection bag 11 will not become dislodged and pinch off the fluid flow. This, it is preferred to secure the collection bag at both ends. Although the use of hooks 121 to secure the collection bag 11 within the housing 110 is preferred, other securing mechanisms such as, for example, a clamping mechanism can also be utilized.

Figure 13:
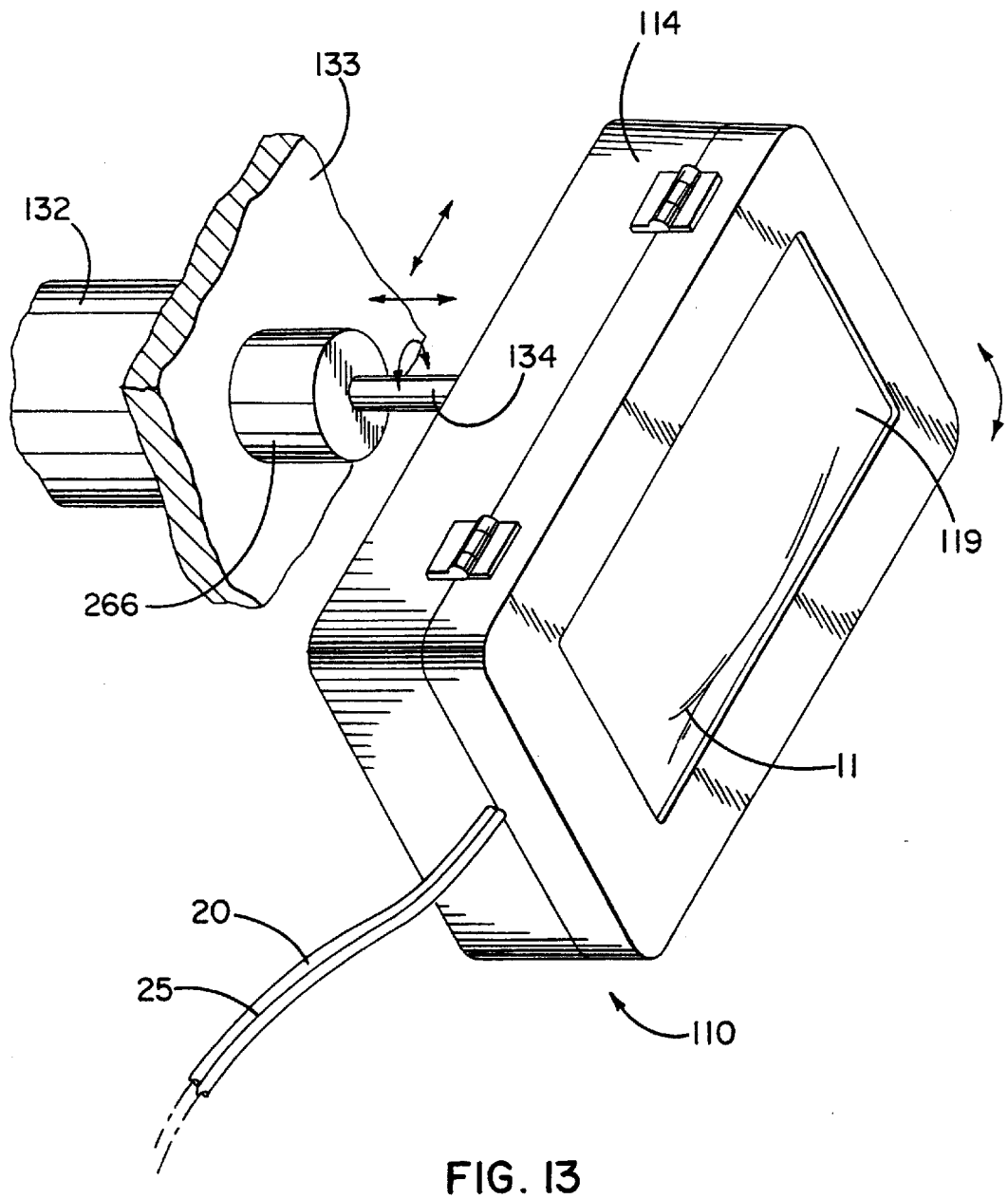
FIG. 13 is a perspective view of a second embodiment of the differential pressure generator according to the invention.

FIG. 13 discloses the housing 110 movably mounted to a support 133 using, for example, a gearing arrangement 266, a motor 132 and a shaft 134. The shaft 134 may be hollow so that pneumatic, hydraulic, or electric supply or control signals may be provided to the housing 110 through the shaft. The motor may be variously configured, for example, as a pulse modulated printed circuit motor, and is preferably coupled to the support 133. The motor 132 may drive the shaft 134 directly, or the motor may be coupled to the shaft 134 using the gearing arrangement 166. Although the illustrated gearing arrangement is external to the motor, it may be incorporated within the motor. The motor and/or gearing arrangement may be configured to oscillate the housing 10 axially along or circumferentially about the shaft 134, or to oscillate the shaft back and forth along an X, Y, and/or Z axis to thereby agitate the fluid in the collection bag 11 by rocking, rotating, oscillating, shaking, and/or vibrating the housing. Of course the apparatus is not limited to a single shaft, gearing arrangement and/or motor arrangement, but may have two or more shaft, gearing, and/or motor arrangements coupled to the housing 110 at, for example, opposite ends.

In a preferred embodiment, the housing 110 is rotated through an angle of about 180 degrees so that the housing 110 may be inverted. The direction of the motor can be reversed so that the housing is rotated back through the same 180 degree rotation. In this manner, the orientation of the housing can be returned to the original position, with the flexible tubing 20, 25 exiting from the upper most portion of the housing 110. By rotating the housing back and forth through the same 180 degree angle, the flexible tubing is prevented from becoming tangled. However, a rotation of less than or greater than 180 degrees is within the scope of the invention. In preferred embodiment, the velocity of the oscillating housing 110 is slowed gradually at either end of the oscillatory movement. This reduces the force acting on the mechanism which secures the collection bag 11 within the housing 110. The motor 132 is electrically coupled to and controlled by the control unit 50. Additionally, the mechanism for affecting the rotation may be any suitable movement mechanism such as pneumatic, electromagnetic, and/or hydraulic mechanism. The gearing arrangement 266 may contain a suitable gear configuration, e.g., a double helix configuration, so that the housing 110 is rotated back and forth through the same angle. The control unit 50 may receive a feedback signal from the gearing arrangement 266 or motor 134 so that the housing 110 may be stopped in one or more positions along its rotation. Additionally, the gearing arrangement 266 may contain one or more locking mechanisms, electronically which may be controlled by the control unit 50, for locking the housing 110 in one or more positions.

In a preferred mode of an expressing operation, the collection bag 11, such as a flexible bag containing a biological fluid, is mounted to the base 112 of the housing 110 with the flexible tubing 20, 25 extending through the opening 117. The collection bag 11 is preferably fixed at both the top and bottom using hooks 121. The cover 113 is then sealed to the base 113 so that the collection bag 11 is completely enclosed within the chamber 111 and enveloped by the housing 110. The housing 110 is then oriented in a desired direction by the control unit 50 using, for example, the motor 132. If the collection bag 11 contains whole blood which has been centrifuged to form sediment and supernatant layers, the housing 110 is preferably oriented vertically with the supernatant layer between the sediment layer and the flexible tubing 20, 25. The housing may be oriented so that the flexible tubing 20, 25 extends through the upper portion of the housing 110, where the flexible tubing 20, 25 communicates directly with any air in the collection bag 11 or with the supernatant layer or the housing may be oriented so that the flexible tubing 20, 25 extends through the lower portion of the housing 110, where the flexible tubing 20, 25 communicates directly with the sediment layer.

With the housing 110 suitably oriented, fluid may be forced from or into the collection bag 11 by supplying or withdrawing fluid from the chamber 111 of the housing 110 by means of the pressure regulating mechanism 130. For example, the pressure regulating mechanism 130 may supply air into the chamber 111, increasing the pressure on the collection bag 11. If the flexible tubing 20, 25 extends from the upper portion of the housing 110, the increase in pressure within the chamber 111 will first force any air and then the supernatant layer from the collection bag 11 via the flexible tubing 20, 25. The interface between the supernatant layer and the sediment layer may be observed through the window 119 and it will rise as the supernatant layer is expressed from the collection bag 11.

The fluid pressure inside the chamber 111 will be substantially uniform throughout the chamber 111, so the outer surface of the collection bag 11 will be exposed to substantially uniform pressure. As a result, the collection bag 11 will be subjected to much less wrinkling, folding, or other forms of distortion than in conventional mechanical expressors or pressure cuffs. Because the collection bag develops fewer wrinkles or folds and because fluid pressure is applied to the entire external surface of the collection bag 11, substantially all of the fluid in the collection bag 11 can be expressed form the collection bag 11 rather than trapped in the folds and wrinkles. In addition, when the collection bag 11 contains centrifuged blood, the uniform external pressure applied to the collection bag 11 tends not to disturb the buffy coat interface.

When an even pressure is applied to the exterior of the collection bag 11, a problem may arise in that as fluid is expressed from an outlet portion 147 of the collection bag 11 adjacent to the flexible tubing 20, 25, the opposing sides of the outlet portion 147 of the collection bag 11 may tend to collapse toward one another. This interferes with the flow of fluid from the collection bag 11 through the flexible conduit 20, 25 and extends the time necessary to completely express the fluid.

It was found that by positioning or pressing an object and/or directing a force against a portion of the collection bag 11, preferably a portion located substantially away from the outlet portion 147 of the collection bag, the fluid in the collection bag 11 is moved within the collection bag 11 and urged towards the outlet portion 147 of the collection bag 11, maintaining the opposing sides of the collection bag 11 spaced from one another. The object and/or force provides a means to move the fluid within the collection bag 11 and urge the fluid toward the outlet portion 147 of the collection bag 11. Urging the fluid towards the outlet portion 147 of the collection bag 11 prevents the uniform external pressure exerted on the collection bag 11 from collapsing the outlet portion 147 of the collection bag 11. A plurality of arrangements are suitable for applying an object and/or a force to the collection bag 11, including a bladder, a spring, a rigid or resilient foam block, and/or a pneumatic, hydraulic, or electromagnetic arrangement.

Figure 28:
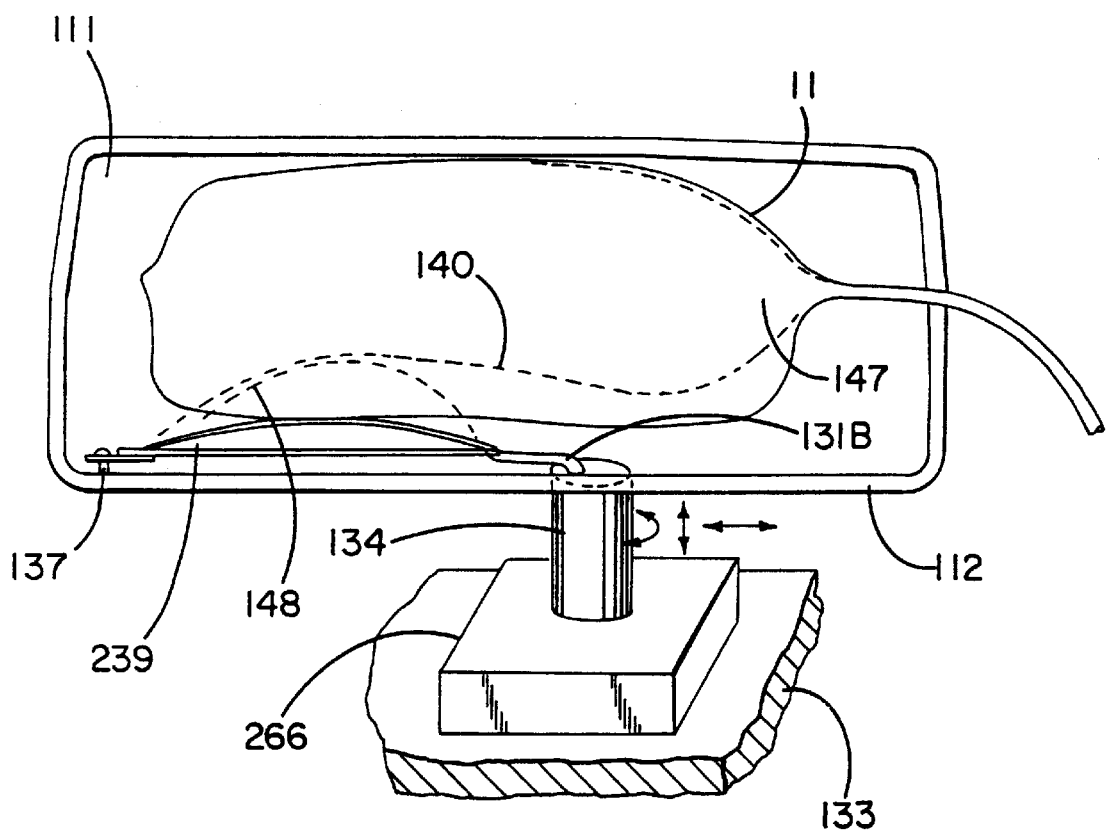
FIG. 28 is a partially cross-sectional view of a preferred embodiment of an pressure differential generator according to the invention.
Figure 29:
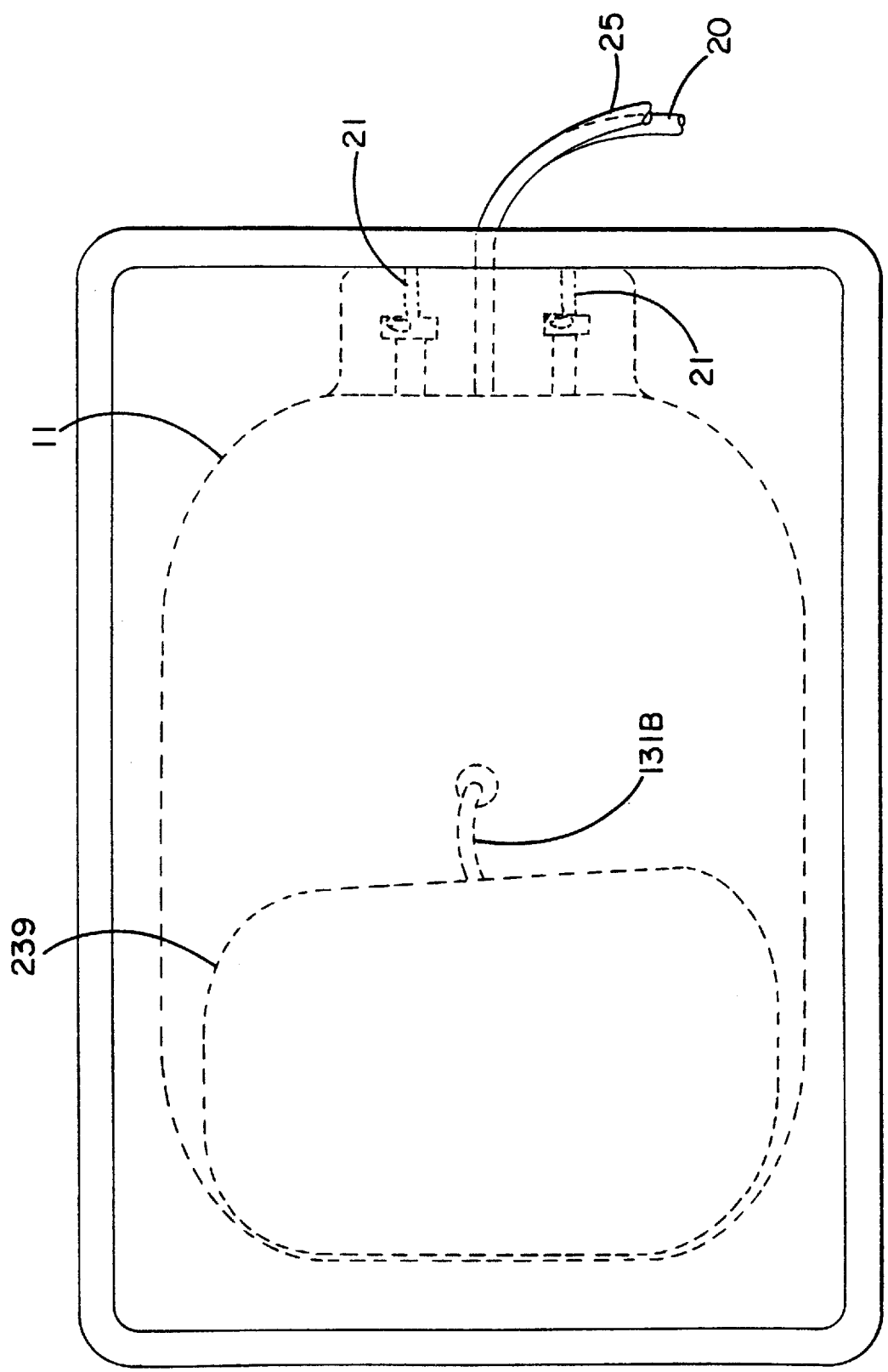
FIG. 29 is a top view of the preferred embodiment shown in FIG. 28.
Figure 30:
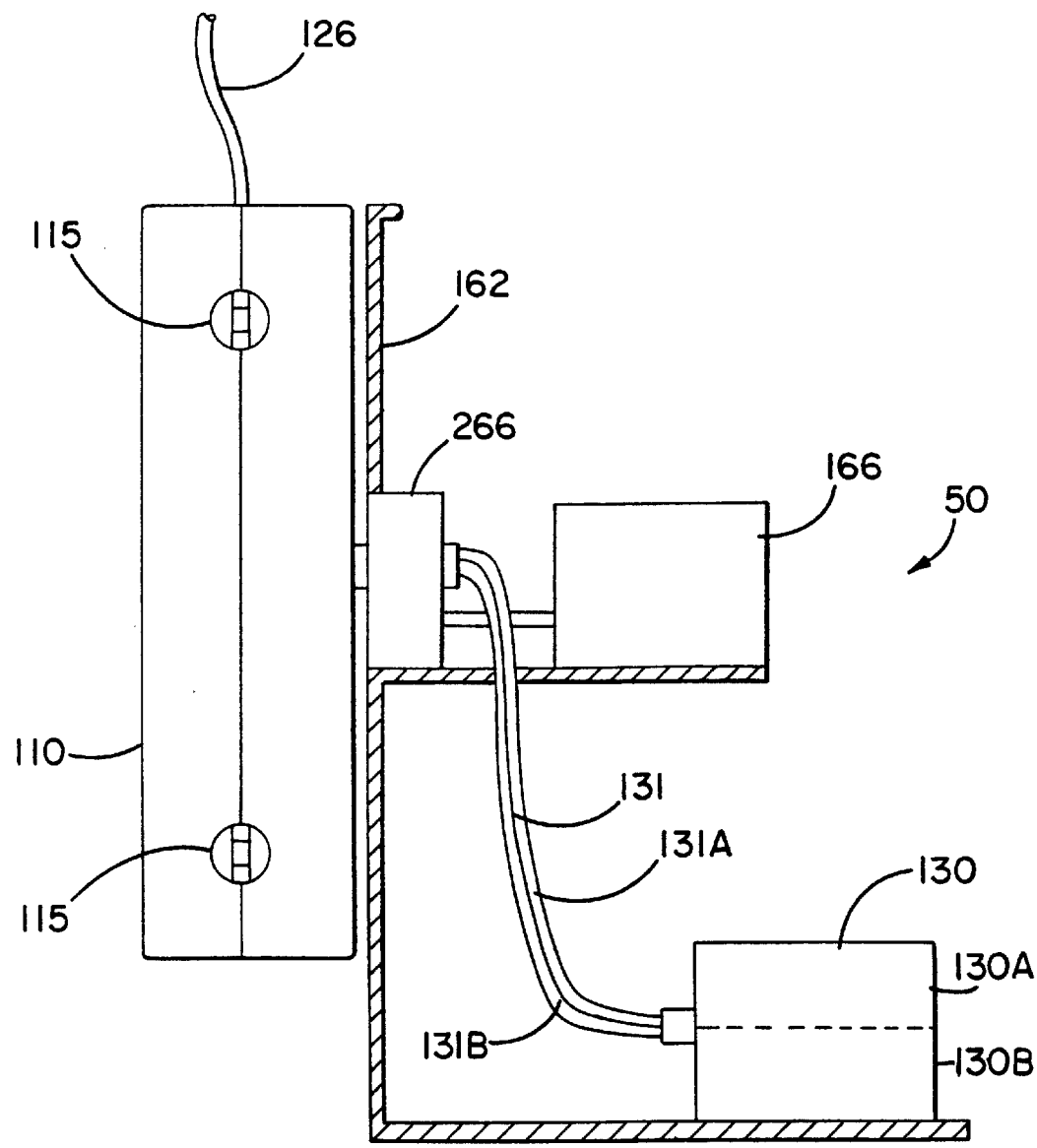
FIG. 30 is a partial cross-sectional view of the preferred embodiment of the pressure differential generator coupled to a portion of a control unit.

Referring to FIGS. 28–30, a preferred embodiment of an expressor containing an arrangement for moving fluid within the collection bag 11 to resist collapse of the outlet portion 147 of the collection bag 11 during expression is shown. At least one bladder 239 is disposed within the enclosed chamber 111, preferably at a location substantially away from the outlet portion 147. Additionally, the bladder 239 is preferably disposed adjacent to only a portion of the collection bag 11, e.g., the portion, such as the lower portion, which is away from the outlet portion 147. The bladder 239 may be attached to the housing 110 using any suitable mechanism, such as an adhesive or a connector. The bladder 239 may be pneumatically coupled to a pressure regulating mechanism 130 via a flexible hose 131 which extends through the shaft 134 or through a separate opening in the housing 110. FIG. 30 discloses a pressure regulating mechanism 130 containing a first section 130A for regulating the pressure of the enclosed chamber 111 and a second section 130B for regulating the pressure of the bladder 239. The first pressure regulating section 130A is coupled to the enclosed chamber 111 via a first flexible hose 131A and the second pressure regulating section 130B is coupled to the bladder 239 via a second flexible hose 131B. The first and second pressure regulating sections 130A, 130B are preferably independently controlled by the control unit 50.

In operation, the pressure regulation mechanism 130 supplies air to the bladder 239, preferably under control of the control unit 50. As the bladder 239 expands, it contacts the portion of the collection bag 11 away from the outlet portion 147 and applies a force against the collection bag 11. This force causes fluid within the collection bag 11 to move within the collection bag 11 toward the outlet portion 147, and thereby maintains the opposing sides of the collection bag 11 spaced from one another as described above. The control unit 50 may control the operation of the bladder 239 so that the bladder 239 expands to any suitable dimension or size at any suitable time in a sequence. The control unit 50 may also control the deflation of the bladder, for example, by opening a relief valve coupled to the bladder 239 and allowing the pressure within the enclosed chamber 111 or the weight of the collection bag 11 to deflate the bladder 239. Alternatively, the control unit may draw a vacuum on the inflated bladder and maintain the vacuum even after the bladder 239 deflates, ensuring that the bladder 239 remains flat. The pressure within the bladder 239 may be increased/decreased with respect to the pressure in the enclosed chamber 111 so that the bladder inflates/deflates properly. Also, the volume of air in the housing may be adjusted to maintain a constant pressure on the bag 11 as the bladder 239 inflates or deflates.

In alternative embodiments, the bladder may include more than one section and/or compartment, and individual sections and/or compartments may be independently operated (e.g., inflated and deflated) in a similar manner. Multiple bladders spaced within the enclosed chamber 111, may be controlled by the control unit 50 to move the fluid within the collection bag 11. The bladder may even be used to express fluid from the container 11, obviating pressurization of the housing 110.

In some embodiments, it may be desirable to mix the contents of the collection bag 11. In a preferred mode of the optional mixing operation, the expressor is capable of moving fluid within the collection bag 11 to mix a plurality of fluids contained in the collection bag 11. Mixing a biological fluid, particularly the mixing of, for example, a preservative solution with PRC, may be automated in accordance with the invention. A plurality of techniques have been developed in accordance with the invention which have reduced the mixing time from, for example, over ten minutes to two minutes or less. In preferred embodiments, the mixing time is less than about one minute and more preferably in the range of 15–30 seconds or less. As will be described in more detail below, the mixing operation may comprise oscillating, rotating, rocking, and/or inverting the collection bag 11. The mixing operation may also comprise kneading the collection bag using one or more bladders. In a preferred embodiment, the housing 110 containing the collection bag 11 is oscillated, rotated, rocked and/or inverted about the shaft 134 to mix the fluid in the collection bag. For example, rotating or rocking the collection bag about the shaft 134 at a rate of about once every 1–2 seconds may be suitable.

Figure 14:
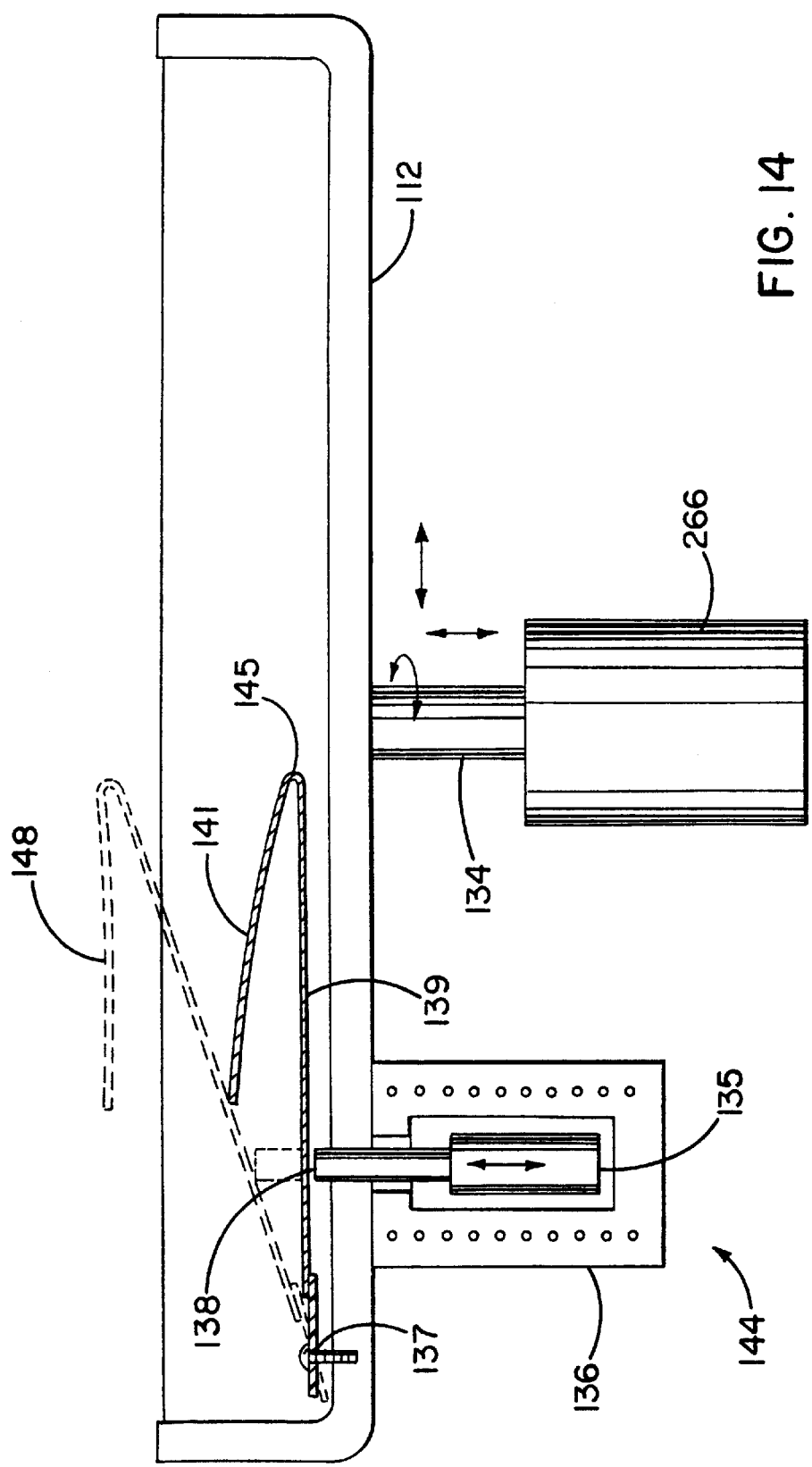
FIG. 14 is a partially cross-sectional side elevation of a third embodiment of the differential pressure generator according to the invention.
Figure 15:
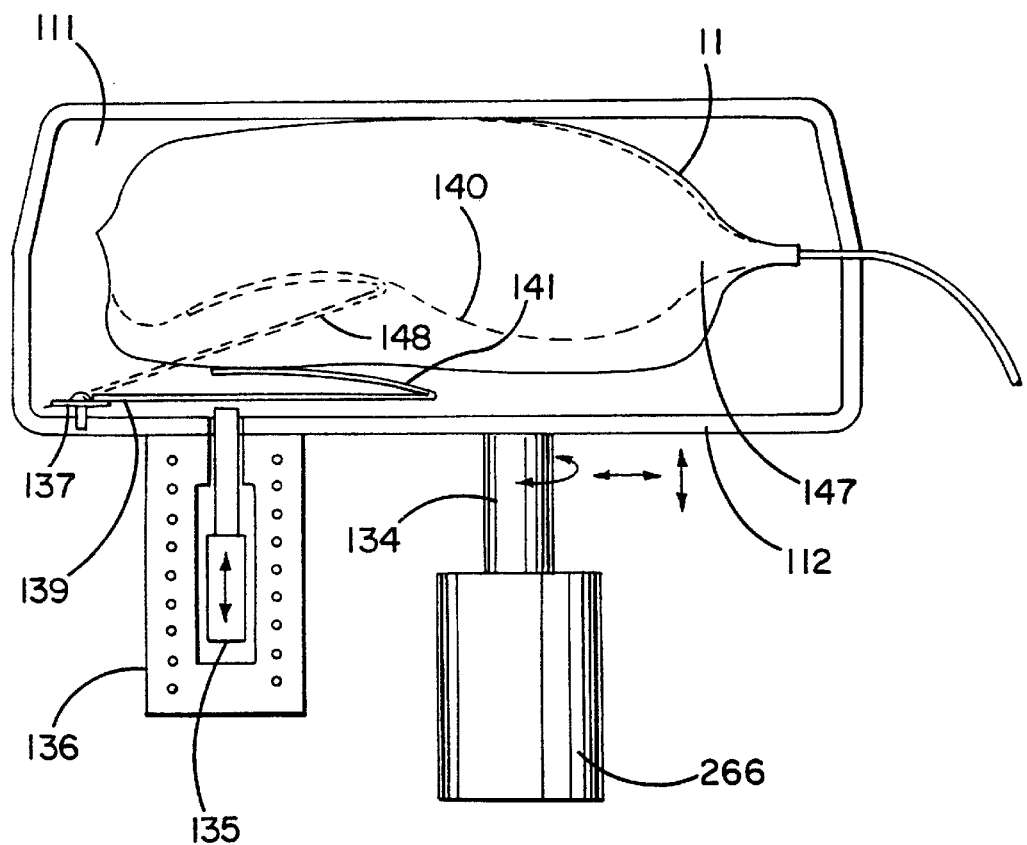
FIG. 15 is a partially cross-sectional side elevation of the third embodiment of the differential pressure generator of FIG. 14.
Figure 16:
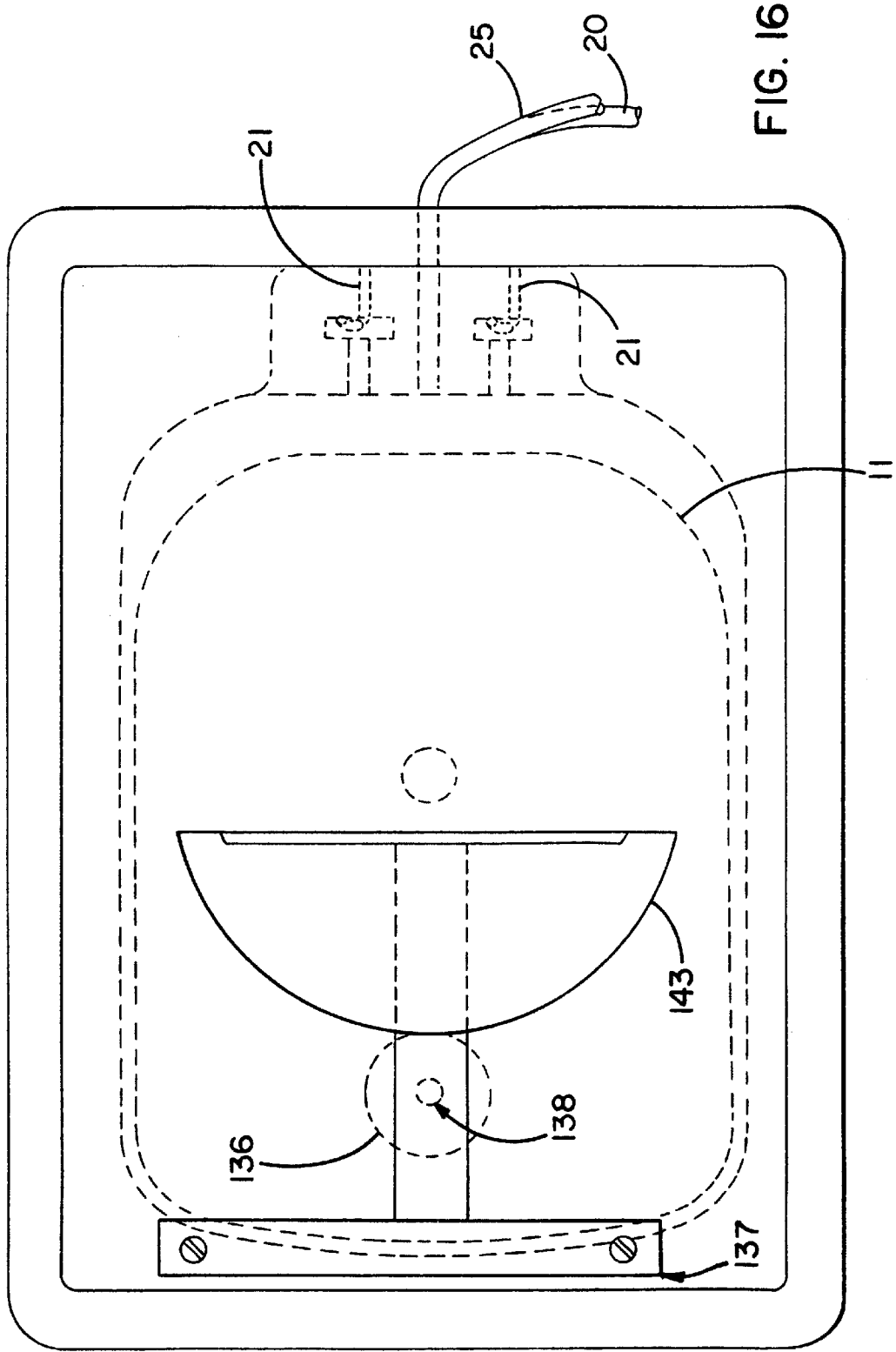
FIG. 16 is a top view of the third embodiment of the differential pressure generator of FIG. 13.

FIGS. 14–16 disclose a second exemplary embodiment of an arrangement for moving fluid within the container 11 to resist collapse of the outlet portion 147 of the collection bag 11 during expression and to promote complete and uniform flow of the fluid from the collection bag 11, as well as moving fluid within the collection bag 11 to mix various fluids contained in the collection bag 11. A solenoid 144 includes a coil 136 surrounding and electromagnetically coupled to a plunger 135. The solenoid 144 may be electrically connected to and controlled by the control unit 50. The plunger 135 is coupled to a shaft 139 at a connecting point 138. The shaft 139 is pivotally connected at a first end to a pivot 137 so that the shaft may rotate about the pivot 137 as shown by dotted line 140. At a second end, the shaft 139 is connected to a paddle 141. The connection 145 may be a rigid connection, a resilient connection, or a biased connection, e.g., where a spring biases the paddle away from the shaft. The paddle 141 may have any suitable configuration, but is preferably semicircular, and it may be dimensioned so that it does not extend across the full width of the collection bag 11. When the solenoid 144 is actuated by the control unit 50, it serves as a drive mechanism, pushing the plunger 135 into the enclosed chamber 111, causing the shaft 139 to rotate about the pivot 137, and moving the shaft 139 and paddle 141 into the position shown by the dotted line 140.

As shown in FIG. 15, when a full collection bag 11 is placed in the enclosed chamber 111, the paddle 141 and the shaft 139 are compressed against the back of the base 112 and the plunger 135 is pushed into a fully retracted position within the solenoid 144. As fluid in the collection bag 11 is expressed and flows out of the collection bag 11 through the conduit 20, 25, the paddle 141 presses or bears against the collection bag 11.

It was found that in some embodiments, the time required to express fluid from the collection bag 11 could be reduced by the application of the solenoid force, as fluid continues to be expressed from the collection bag 11. The force of the solenoid 144 compensates for the additional fluid that has been expressed from the collection bag 11, without requiring a large spring that may render insertion of the collection bag 11 in the enclosed chamber 111 difficult. As the plunger 135 is forced out of the solenoid, the action of the solenoid-driven paddle 141 upon the fluid in the collection bag 11 serves to prevent collapse of the outlet portion 147 of the collection bag 11, even as the supernatant layer is expressed from the collection bag 11. The position of the collection bag 11 relative to the housing 110 before and after the actuation of the solenoid 144 is shown in FIG. 15. The dotted lines 140 and 148 respectively represent the position of the collection bag 11 and the paddle 141 after the solenoid 144 has been actuated.

Using the solenoid 144 and paddle 141 to repeatedly press against the container 11 in conjunction with oscillating, rotating, rocking and/or inverting the collection bag 11 as described above may further facilitate mixing the fluid in the collection bag 11. For example, the solenoid may be actuated by the controller 50 at a frequency of, for example, 1–5 cycles per second. The solenoid 144 is preferably actuated using a square wave pulse of a relatively short duration.

FIGS. 24–27 disclose a third exemplary embodiment of an arrangement for moving fluid within the container to resist collapse of the outlet portion 147 of the container 11 and/or to mix fluid in the container 11. The expressor includes the collection bag 11, a roller or a non-rolling kneader fist 201 located within the housing 110, and a motor 166 which serves as a drive mechanism to actuate the kneader fist 201. The mechanism for effecting the movement of the kneader fist 201 is unimportant, and any suitable movement mechanism such as pneumatic, electromagnetic, and/or hydraulic mechanism may be utilized as a means for moving the kneader fist 201 in place of the motor 166. The motor 166 or other movement mechanism may be fixed to the housing 110 using any known technique, e.g., a motor mount 206. The motor mount 206 is shown in detail in FIG. 26. A shaft 234 of the motor 165 is fixedly coupled to a reversing ball screw 205, which is preferably configured in a double helix configuration. A ball nut 204 is slideably coupled to the reversing ball screw 205. A kneader block 203 and the kneader fist 201 are fixedly coupled to the ball nut 204 and move with the ball nut 204 along the reversing ball screw 205. Tracks 211, formed in a separating plate 207, extend parallel to the ball screw 205 and guide the kneader fist 201 and the kneader block 203 as they move along the reversing ball screw 205. The kneader fist 201 and the kneader block 203 are shown in detail in FIG. 27.

In operation, actuation of the motor 166 causes the reversing ball screw 205 to rotate, and consequently results in a linear back-and-forth movement of the ball nut 204, the kneader block 203, and the kneader fist 201. The motor 166 may be coupled to and controlled by the control unit 50 and may receive power and control signals from the control unit 50 through a hollow portion of shaft 134. The motor 166 may be operated in a continuous fashion for achieving the mixing operation as described above, preferably as the housing 110 is oscillated along the shaft 134. Alternatively, the motor 166 may be actuated so that the kneader fist 201 is moved along the reversing ball screw until it is brought into contact with, land presses against, the collection bag 11 to prevent the outlet portion 147 of the collection bag 11 from collapsing. The control unit 50 may receive a feedback signal from the gearing arrangement 266 or motor 166, 132 so that the housing 110 may be stopped in one or more positions along the rotation or the kneader block 203 may be stopped at one or more locations along the reversing ball screw 205. Additionally, the gearing arrangement 266 and reversing ball screw may contain one or more locking mechanisms, electronically controlled by the control unit 50, for locking the housing 110 and/or kneader block 203 in one or more positions.

A preferred automated biological fluid processing system 149 may be configured, for example, as shown in FIG. 17. The control unit 50, may for example, include a user interface, such as a keyboard 150, a display 151, a program/data entry medium such as a magnetic storage disk 152, and/or a scanner 170. The control unit 50 is also coupled to flow meter 72.

The flow meter 72 is preferably similar to the flow meter described in U.S. application Ser. No. 07/589,523 filed on Sep. 28, 1990 and EPO Publication 0477973 published on Apr. 1, 1992. The flow meter 72 may be a differential flow meter that measures the rate of fluid flow into or out of a container by measuring the rate of change of the weight of the container. The flow meter typically includes a weight transducer coupled to a differentiating mechanism and a control unit. The weight transducer preferably is a structure suitable for producing a signal proportional to a weight placed upon the structure. The container may be placed directly on the structure or the container may be placed in the housing 110 of an expressor which, in turn, is placed on the structure. The differentiating mechanism produces a signal proportional to a rate of change of a weight placed on the load cell and bearing the strain gauges. The control unit may determine the absolute weight of an object by directly sampling the output signal from the weight transducer, or the control unit may determine the rate of flow of fluid to or from the weight transducer by sampling the signal from the differentiating mechanism. When such a flow meter is used in conjunction with the automated blood processing system, it is possible to determine both the total quantity and the rate of flow of a fluid.

A block diagram of the preferred biological fluid processing system 149 is shown in FIG. 18. FIG. 18 is similar to FIGS. 1 and 2 in construction and operation, and identical reference numerals refer to identical parts. The collection bag 11, or any other fluid container, may be mounted within the differential pressure generator 51. Flexible tubing 20, 25, 28 interconnects a plurality of containers 11, 18, 41, 42. Valves 61–64 are electrically coupled to the control unit 50.

The operation of a preferred embodiment of the automated biological fluid processing system 149 shown in FIGS. 17 and 18 in accordance with the invention may be illustrated by reference to the flow charts shown in FIGS. 19–22. Prior to initiation of a particular operation sequence, a biological fluid is typically collected into the collection bag 11, which is connected by conduits to at least one satellite container. The collection bag 11 is then centrifuged to form a supernatant layer and a sediment layer. The collection bag 11 then is placed in the differential pressure generator 51, the conduits associated with each of the satellite containers are connected to valves 61–64 and the satellite bags 18, 41, 42 are placed on the flow meter 72. In a preferred embodiment, the collection bag 11 contains whole blood which has been separated into a supernatant PRP layer 31 and a sediment PRC layer 32.

Figure 19:
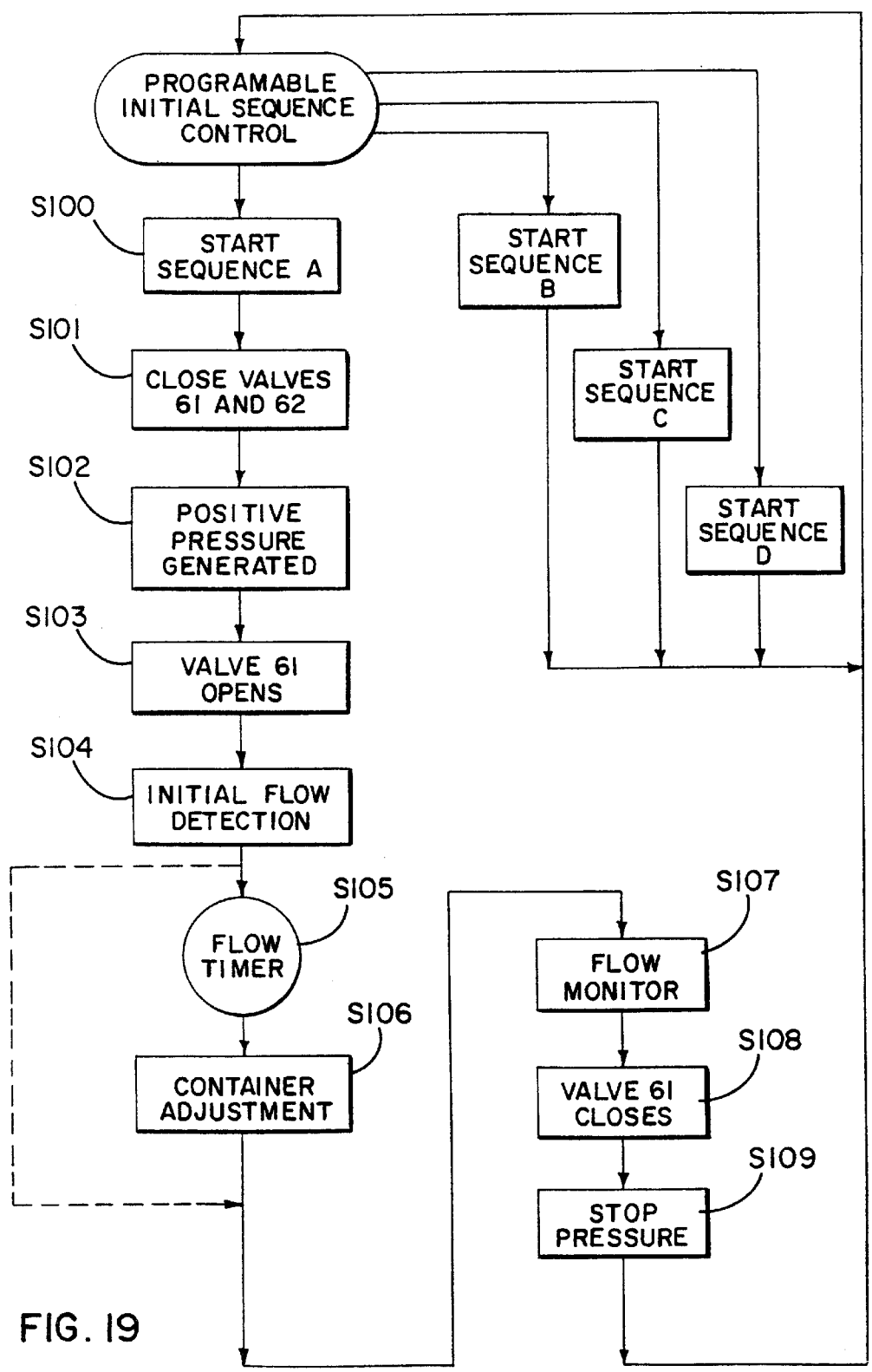
FIG. 19 is a flow chart of an exemplary sequence according to the invention.
Figure 20:
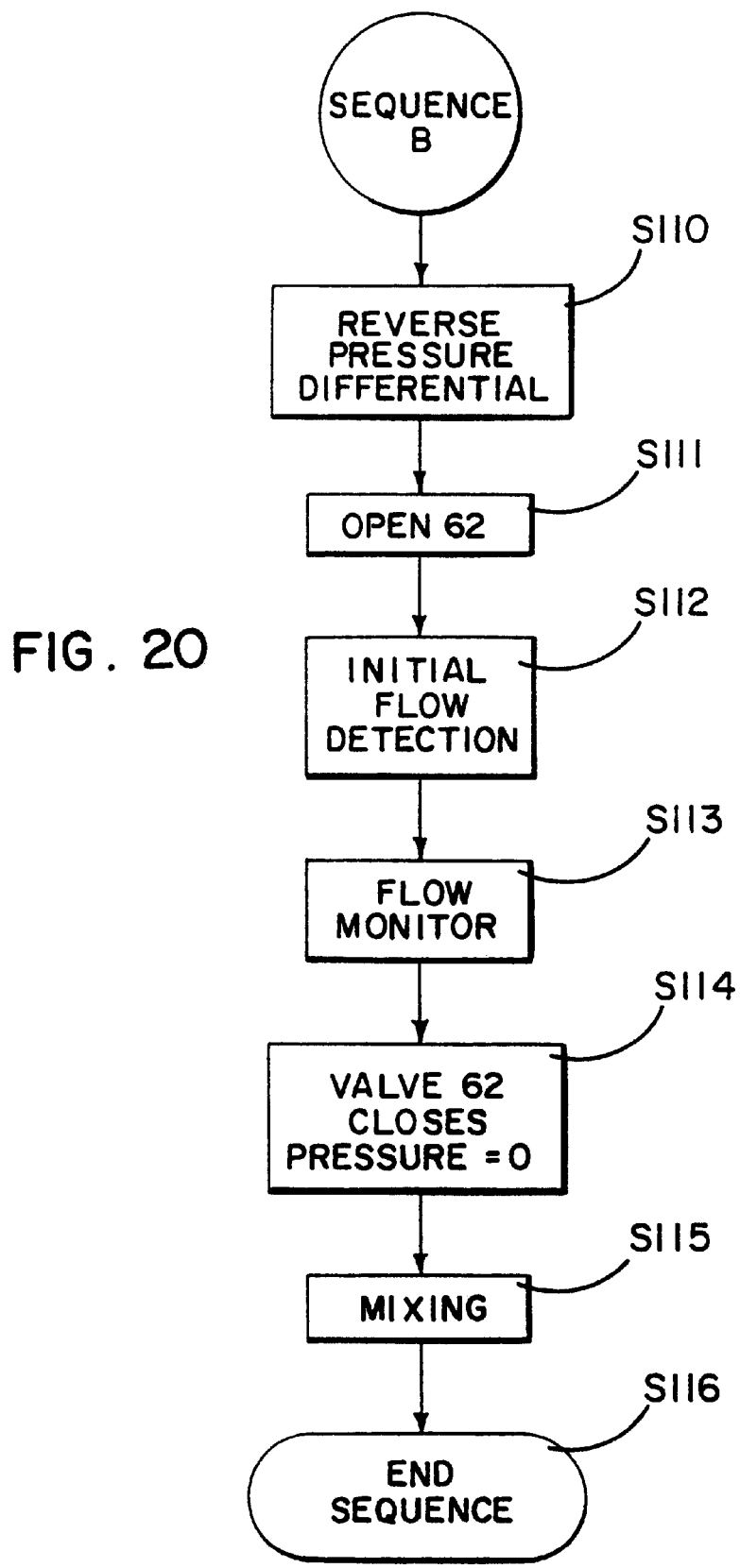
FIG. 20 is a flow chart of an exemplary sequence according to the invention.

FIG. 19 discloses a programmable initial sequence control block. In this block, a program in the control unit 50 can select any number and combination of sequences for processing biological fluids. The particular sequences and parameters within the sequences are programmed to correspond to, for example, the fluids to be processed, the filter types and sizes in the system, the size of the fluid containers, the length of the tubing, the type and quantity of preservative contained in the fluid containers, and the quantity of the desired fluid to be obtained. If desired, this information, and any other selected information, e.g., donor identification information, may be collected using any suitable input, e.g., scanner 170, and processed for inventory control.

In some embodiments, it may be desirable to track and/or monitor the biological fluid as it is processed according to the invention, e.g., to automatically provide information to the operator and/or the end user(s) of the biological fluid. Accordingly, information relating to the source of the biological fluid, such as the donor or source batch identification, the blood type, the weight of the donated unit may be manually or automatically entered into the control unit using, for example, the scanner 170 and/or other portions of the user interface means. The information may be stored in the control unit 50 and made available as desired. Additionally, as the biological fluid is processed, additional information, for example, the additive solution and/or the viricidal agent used, the level of leukocyte depletion, the final weight of the processed fluid, the number of units processed by a particular operator and the time period required to process a particular unit, etc., may also be processed by the control unit 50.

In an exemplary embodiment, the biological fluid may be processed according to the invention to produce PRC, PC and plasma in separate containers, and a label including some or all of the above information may be manually or automatically generated, for example using a label printer 253, at the appropriate time to be placed on the appropriate container. In a preferred embodiment, the container of donated biological fluid may include a bar code label encoding the appropriate source information, so that the use of the scanner 170 allows the automatic entry of the information before the biological fluid is processed according to the invention. This has the advantage of minimizing the risk of operator error in initiating the correct processing sequence for control unit 50.

Among other advantages, the information associated with a particular fluid container may be used as part of an inventory control and/or tracking system. In this regard, a plurality of control units 50 may be connected together with one another, and with a centralized data base, which, may also be interfaced to one or more user locations.

Integrating an inventory control and tracking system into the control unit 50 has many advantages, including minimizing the possibility that the wrong unit may be used during a medical procedure.

In some embodiments, it may be preferable to pool a number of units from a plurality of containers. In this case, it may be desirable to identify the source of all fluids that have been pooled. When pooling is being performed by the control unit 50, the control unit may provide a detailed label identifying the sources of the pooled biological fluid as well as any processing and handling steps that have occurred relative to the pooled or source biological fluid.

Additionally, the control unit 50 may incorporate various fail-safe programs to ensure that an alarm is indicated if a particular biological fluid is processed using an improper processing sequence. Control unit 50 may also be programmed to provide a warning if an incorrect amount of one or more components of the processed biological fluid is produced.

In a preferred embodiment, the control unit 50 is programmed to respectively initiate sequences A, B, C, and D shown in FIGS. 19–22 for separating the components of a biological fluid such as whole blood. The operator would instruct the control unit as to the proper sequence using a user interface means, such as display 250, disk drive 152, and/or keyboard 150. After the collection bag 11 and any satellite bags 18, 41, 42 have been correctly positioned, the operator initiates the control sequence by, for example, pressing a start button.

In step 100 (hereinafter, S101, S102, S103, etc.), sequence A is started. The control unit 50 verifies that there is a stable flow, e.g., 0 ml/minute, for a predetermined time period such as 3 seconds. This initial check can be utilized to calibrate the flow meter 72 and control unit 50 to a zero flow condition. The initial check for zero flow verifies that the system has stabilized after the flexible tubing 20, 25, 28 and the satellite bags 18, 41, 42 have been placed on the flow meter 72 by the operator. If the flow has not stabilized, the operator is notified via the user interface means, such as display 250. The display may be utilized in conjunction with an audible indication or other means of notifying the operator of anomalous conditions.

In S101, valves 61 and 62 are closed. Alternatively, the valves may be closed as the first step in the initialization of sequence A.

In S102, a differential pressure is generated between the collection bag 11 and the satellite bag 41 by, for example, pressurizing the enclosed chamber 111 of the pressure differential generator 51. The flow meter 72 may be checked to ensure that the flexible tubing 20, 25 has been correctly inserted into clamps 61 and 62, respectively, and that clamps 61 and 62 are functioning correctly. Thus, the control unit 50 verifies that a stable flow, e.g., 0 ml/minute, is maintained even after the differential pressure is generated. In the expression of PRP through a porous medium such as a red cell barrier medium, it was found that a differential pressure of approximately 2 psi provides optimum results with respect to expression time, effectiveness of the filter medium, and the ability to detect that the PRP layer has been completely expressed.

In S103, valve or clamp 61 is opened, and the pressure differential between the collection bag 11 and the first satellite bag 41 causes the supernatant PRP layer 31 to flow in the direction of the satellite bag 41. As the supernatant PRP layer 31 passes from the collection bag 11 to the first satellite bag 41, it typically passes through at least one porous medium, preferably a red cell barrier medium or combined leukocyte depletion and red cell barrier medium.

It is preferable to close both valves 61 and 62 prior to the initiation of the differential pressure. It may also be preferable for the control unit 50 to monitor the pressure in the pressure differential generator 51 to ensure that a sufficient pressure has been established prior to opening clamp 61 in S103. The establishment of a sufficient pressure differential, combined with the sudden opening of valve 61, results in a column of biological fluid which pushes a column of air through the porous medium and then allows the column of biological fluid to impact the porous medium suddenly. This sequence of operation results in optimum performance and is particularly important for optimal operation of the porous medium. If valve 61 is left open so that the biological fluid is pushed through the tubing slowly as the pressure is increased, air bubbles become trapped in the fluid, and the efficiency of the porous medium is reduced. Thus, in the preferred operation the valves 61, 62 are closed prior to establishing the differential pressure and the valve 61 is suddenly opened.

In S104, an initial flow detection is performed. The flow of the supernatant layer is monitored to ensure that the valve 61 has been properly released and that the flexible tubing 20 is not obstructed. The initial flow detection performs a check to verify that the flow exceeds a first predetermined level. if the initial flow rate is too low, the operator may be notified via the user interface means, or the differential pressure may be adjusted. Once the first predetermined level of initial flow has been detected, S105 is initiated.

In S105, the flow is monitored until either a predetermined quantity of fluid has been expressed from the collection bag or until a predetermined time period has elapsed from when the initial flow exceeded the predetermined level. In a typical application, the predetermined time period is set, for example, at between 3 to 5 minutes and the predetermined quantity may be set, for example, at between about 100 and about 120 cc.

In S106, the control unit 50 may cause a force to be applied against the collection bag 11. As previously discussed, the force may be applied by, for example, the bladder 239, the paddle 141, or the kneader fist 201. In a preferred embodiment, the control unit 50 actuates the bladder 239 by having the second section 130B of the pressure regulating mechanism 130 increase the pressure within the bladder 239 to a level which exceeds the pressure of the enclosed chamber 111. Increasing the pressure within the bladder 239 forces an exterior surface of the bladder 239 against the collection bag 11. In this manner, the fluid in the collection bag 11 is moved so as to prevent the outlet portion 147 of the collection bag 11 from collapsing as previously discussed. However, step S106 may be omitted if desired. If this step is omitted, processing proceeds directly to S107.

In S107, the flow is monitored until the flow decreases below a second predetermined level. When the flow has fallen to the second predetermined level, the control unit 50 determines that flow should cease.

The first and second predetermined levels may be variously selected depending on a particular application. For example, these levels may be a percentage of a maximum expected flow from the container. The first predetermined level may be approximately 50%–75% of the maximum expected flow while the second predetermined level may be approximately 20%–50% of the maximum expected flow. In the preferred embodiment of the invention, a red cell barrier porous medium or a red cell barrier leukocyte depletion porous medium is used, and the monitor produces a signal monitoring the flo rate through the red cell barrier or the red cell barrier leukocyte depletion porous medium. Once the supernatant PRP layer has been completely expressed from the collection bag 11, the red cells near or in the sediment PRC layer contact the red cell barrier medium or the red cell barrier leukocyte depletion medium. Flow through the medium then significantly slows or stops. In one embodiment, where the maximum expected flow is about 40 cc/minute, the first predetermined level may be about 25 cc/minute while the second predetermined level may be about 15–20 cc/minute. Alternatively, where the maximum expected flow is about 20–25 cc/minute, the first predetermined level may be about 10–15 cc/minute while the second predetermined level may be about 4–7 cc/minute.

In S108, the signal produced in S107 causes the control unit 50 to close valve or clamp 61, and eliminate any force, i.e., the bladder 239, the paddle 141, or the kneader fist 201 from bearing against the collection bag 11. In a preferred embodiment, the clamp 61 is closed quickly and the conduit 27 extending from the red cell barrier medium or the red cell barrier leukocyte depletion medium to the first satellite bag 41 is relatively long. Consequently, in the event that any red cells pass through the porous medium, they will be prevented from reaching the first satellite bag 41.

Figure 21:
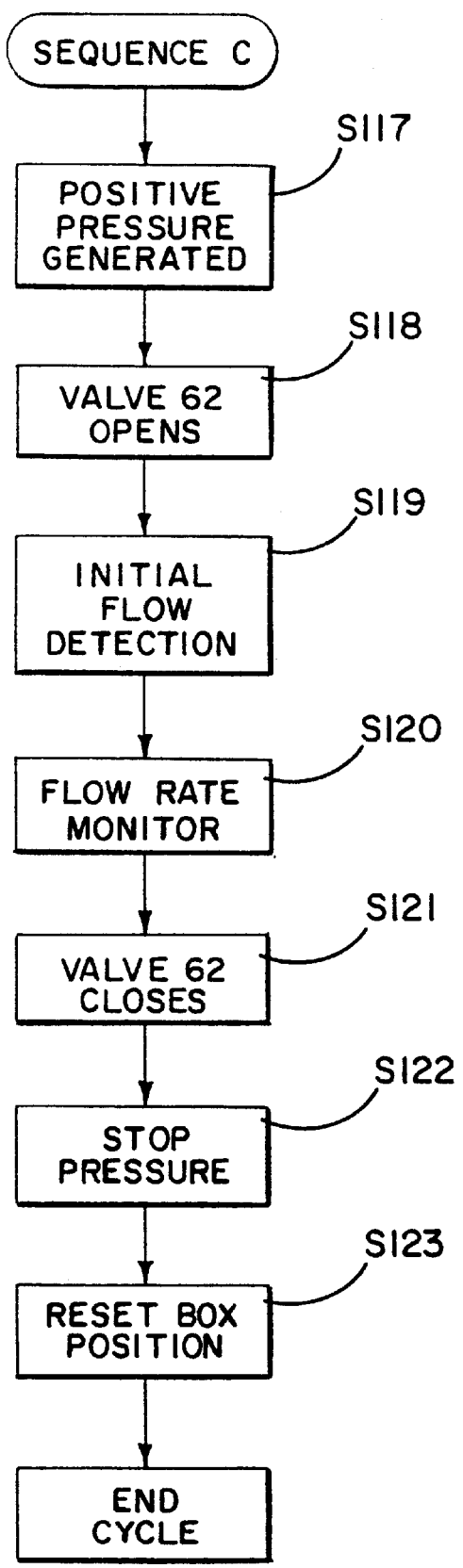
FIG. 21 is a flow chart of an exemplary sequence according to the invention.

In S109, the control unit 50 decreases the differential pressure to zero and returns the sequence control to the programmable initial sequence control block for the initiation of, for example, sequence B as shown in FIG. 21.

Sequence B provides, for example, a mechanism to transfer an additive solution, diluent, preservative, or the like, from a satellite bag into the collection bag 11 and add it to the sediment PRC layer 31 remaining in the collection bag 11 after completion of sequence A. In S109 the collection container is preferably inverted by rotating the pressure differential generator approximately 180 degrees.

In S110, a reverse differential pressure is created for example, by creating a vacuum in the differential pressure generator 51, between the collection bag 11 and the second satellite bag 18 which contains the additive solution. The flow meter 72 may be monitored by the control unit 50 to ensure that the flexible tubing 20, 25 has been correctly inserted into clamps 61 and 62, respectively, and that clamps 61 and 62 are functioning correctly so that a zero flow is indicated.

In the retrieval of the solution from the second satellite bag 18 into the collection bag 11, it was found that a negative differential pressure of approximately 1 psi provides optimum results with respect to retrieval time and with respect to the viscosity of the fluid.

In S111, valve or clamp 62 is opened, and the pressure differential between the collection bag 11 and the second satellite bag 13 causes the solution in the second satellite bag 18 to flow in the direction of the collection bag 11. As the solution passes from the second satellite bag 18 to the collection bag 11, it typically passes through at least one porous medium, preferably a leukocyte depletion medium.

It is preferable to close both valves 61 and 62 prior to the initiation of the differential pressure. It may also be preferable for the control unit 50 to monitor the pressure in the pressure differential generator 51 to ensure that a sufficient pressure has been established prior to opening clamp 62 in S111. As discussed above, the establishment of a preexisting pressure differential, combined with the sudden opening of valve 62, provides enhanced flow of the solution from the second satellite bag 18 to the collection bag 11.

In S112, an initial flow detection is performed. The flow of the solution is monitored to ensure that the valve 62 has been properly released and that the flexible tubing 20 is not obstructed. The initial flow detection performs a check to verify that the flow into the collection container 11 exceeds a predetermined level, e.g., up to 40 ml/minute or more. If the initial flow rate is too low, the operator may be notified via the user interface means, or the differential pressure may be adjusted. Once an initial flow of, for example, at least 40 ml/minute has been detected, S113 is initiated.

In S113, the flow is monitored until the negative flow decreases below a predetermined minimum flow rate, for example, between about 0 and 7 ml/minute into the collection container 11. When the flow has fallen to the minimum predetermined flow rate, the control unit 50 determines that flow should cease. The control unit 50 may then produce a signal indicating that the solution has been transferred from the satellite bag 18 into the collection bag 11. This signal may be used to generate either an audible or visual indication to the operator, e.g., via the user interface means.

In S114, the signal produced in S113 causes the control unit 50 to close valve 62, and shut off the differential pressure generated between the collection bag 11 and the satellite bag 18. In S115, the solution and the PRC are mixed together by oscillating or rocking the collection bag. It has been found that an oscillation frequency of about once a second is sufficient for mixing the contents of the collection bag 11. Of course, a higher or lower oscillation rate could be utilized. Optionally, the mixing of the collection bag 11 may be facilitated by, for example, oscillating, vibrating, and/or shaking the housing 110 and/or collection bag 11 along one or more of the three dimensional axes of movement, pulsating the collection bag 11 using, for example the paddle and/or one or more bladder, and/or kneading the collection bag 11 using the kneader fist 201. If one of the optional mixing mechanisms are utilized, it may be desirable to actuate the mixing mechanism at a relatively high frequency. The control unit 50 preferably continues the mixing process for approximately 2 minutes or less. The mixing time is variable with the quantity of PRC and the particular solution utilized in the mixing process.

In S116, the mixing process is stopped so that the differential pressure generator 51 is located in the inverted position and control is returned to the programmable initial sequence control block for initiation of, for example, sequence C as shown in FIG. 21.

Sequence C serves to express the sediment PRC layer 32 from the collection bag 11 into the second satellite bag 18. In S117, a differential pressure is generated between the collection bag 11 and the second satellite bag 18 by pressurizing the pressure differential generator 51. In the expression of PRC through a leukocyte depletion assembly, it was found that a differential pressure of approximately 1–3 psi provides optimum results with respect to expression time and effectiveness of the porous medium.

In S118, valve 62 is opened and sediment PRC layer 32 in collection bag 11 is preferably passed through a leukocyte depletion assembly 17 and into the second satellite bag 18. As with the previous instances when the valves are opened, it may be desirable to create a pressure differential before opening the valve 62, and for the control unit 50 to verify that the clamp is functioning properly and that a sufficient differential pressure has been generated.

In S119, an initial flow detection is performed. The flow of the sediment layer is monitored to ensure that the valve 62 has been properly released and that the flexible tubing 25 is not obstructed. The initial flow detection performs a check to verify that the flow exceeds a predetermined level, e.g., about 20 ml/minute or more. If the initial flow rate is too low, the operator may be notified via the user interface means, or the differential pressure may be adjusted. Once an initial flow of, for example, at least about 20 ml/minute has been detected, S120 is initiated.

In S120, the flow is monitored until the flow decreases below a predetermined minimum flow rate, for example, between 3 and 7 ml/minute. When the flow has fallen to the minimum predetermined flow rate, the control unit 50 determines that flow should cease.

In S121, the signal produced in S105 causes the control unit 50 to close valve 62.

In S122, the control unit decreases the differential pressure between the collection bag 11 and the satellite bags to about zero.

Figure 22:
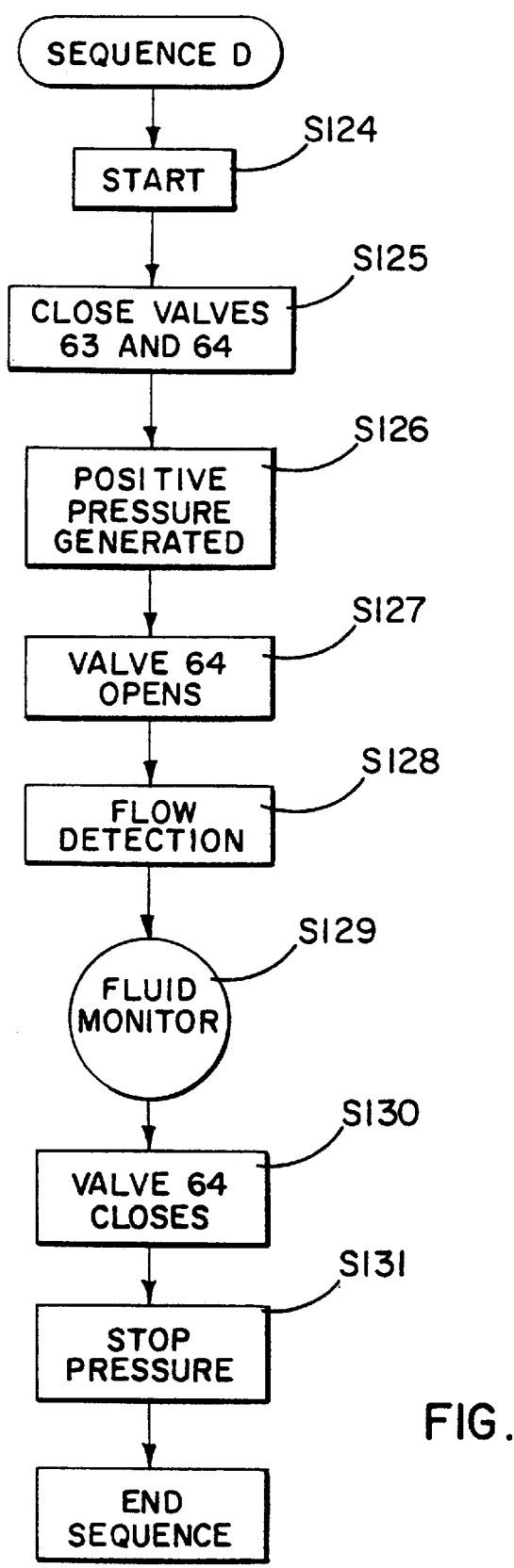
FIG. 22 is a flow chart of an exemplary sequence according to the invention.

In S123, the control unit resets the housing 110 by rotating it through an angle of 180 degrees in the manner discussed above to return the housing to the normal upright or non-inverted position as shown in FIG. 17. Program control is then returned to the programmable initial sequence control block for initiation of another sequence, e.g., sequence D as shown in FIG. 22.

Figure 23:
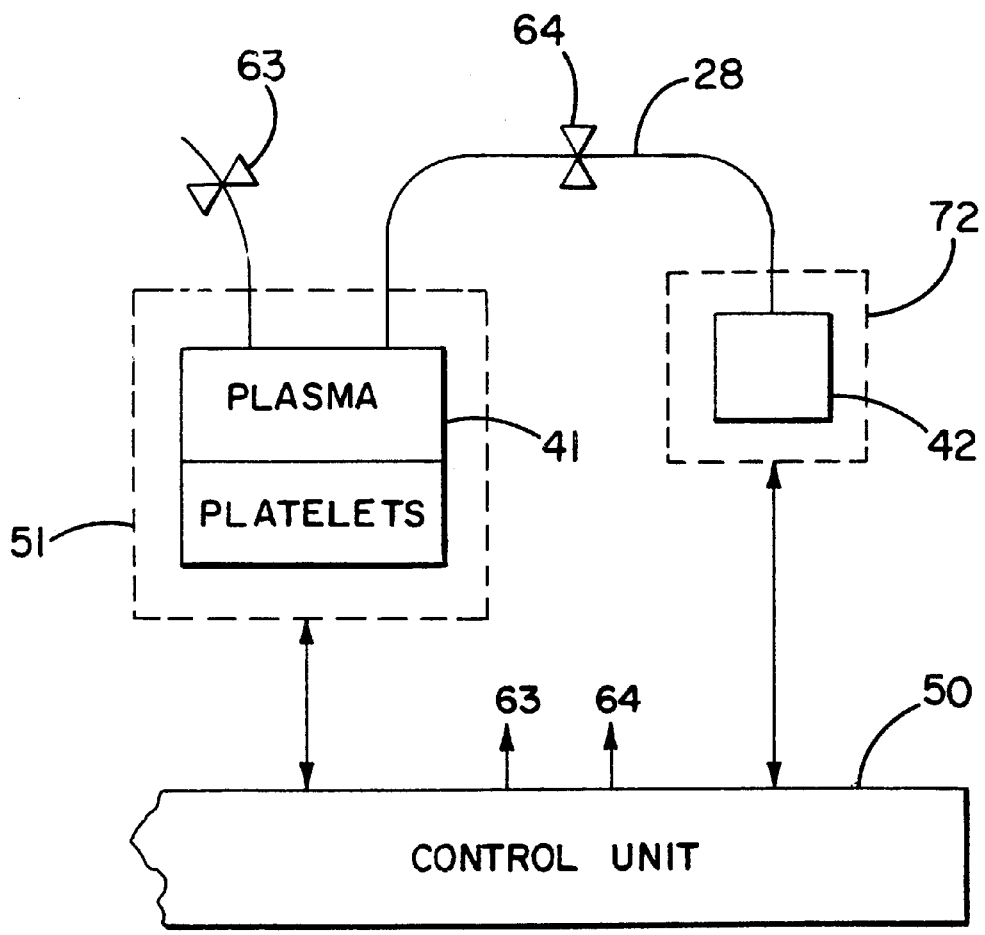
FIG. 23 is a block diagram of an embodiment of a portion of the biological fluid processing system according to the invention.
Figure 24:
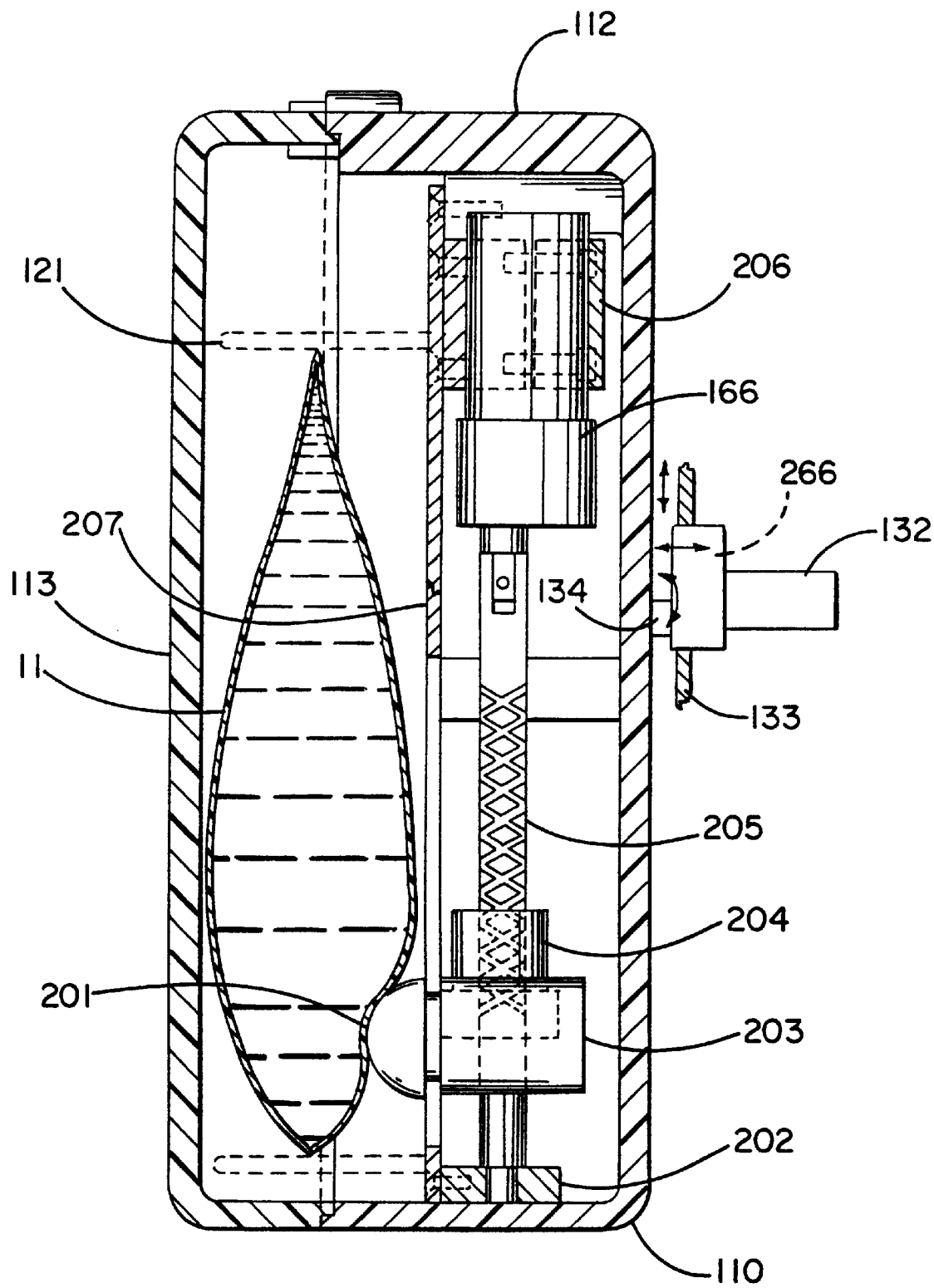
FIG. 24 is a partially cross-sectional view of a fourth embodiment of an pressure differential generator according to the invention.
Figure 26:
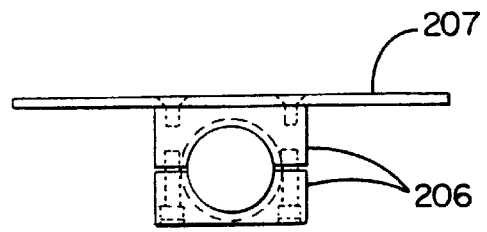
FIG. 26 is a view of a motor mount of the fourth embodiment of FIG. 24.
Figure 25:
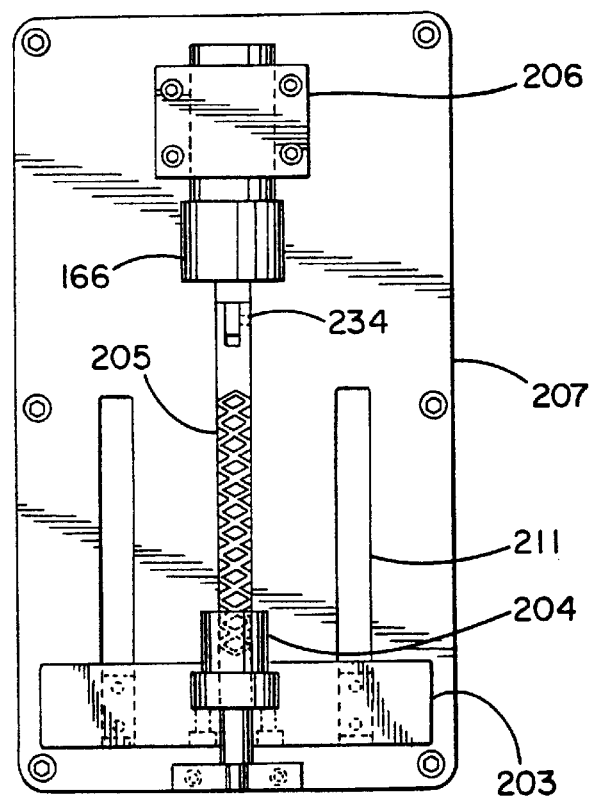
FIG. 25 is a view of the fourth embodiment of FIG. 24.
Figure 27:
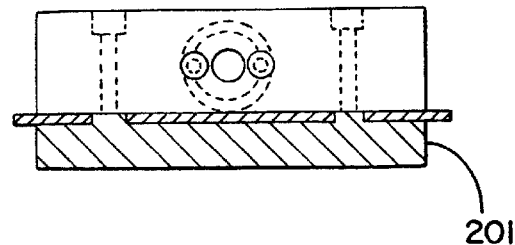
FIG. 27 is a view of a kneader block and a kneader fist of the fourth embodiment of FIG. 24.

Prior to initiation of sequence D, the operator may be prompted by the user interface means of the control unit 500 to remove the satellite bags from the flow meter 72 and to remove the empty collection bag 11 from the pressure differential generator 51. In one embodiment, involving a collection bag 11, first satellite bag 41, second satellite bag 18, and third satellite bag 42, the empty collection bag and the second satellite bag 18 containing the mixture of PRC and additive solution are separated from each other and the remaining two satellite bags. The remaining satellite bags, i.e., first satellite bag 41 (containing the PRP) and the third satellite bag 42 (which is empty) remain in fluid communication. Typically, the first and third satellite bags 41, 42 are placed in a centrifuge and spun to separate the PRP contained in the first satellite bag 41 into a second supernatant layer, typically plasma, and a second sediment layer, typically a platelet containing layer which may be processed to form PC. After centrifugation, the operator places the first satellite bag 41 into the pressure differential generator 51 and the third satellite bag 42 onto the flow meter 72, as shown in FIG. 23. The conduits are located with respect to valves 63 and 64 as shown in FIG. 23. At this time, the operator instructs the control unit 50 to begin initiation of sequence D.

Sequence D serves to separate the supernatant plasma layer from the sediment platelet containing layer. In step 124, the control unit checks to verify that there is a stable flow (e.g., 0 ml/minute) for a predetermined time period such as 3 seconds. This initial check can be utilized to calibrate the flow meter 72 and control unit 50 to a zero flow condition. The initial check for zero flow verifies that the system has stabilized after the conduits 27, 28 and the satellite bags 41, 42 have been placed on the flow meter 72 by the operator. If the flow has not stabilized, the operator is notified via the user interface means.

In steps 125, valves 63 and 64 are closed.

In step 126, a positive pressure differential is generated between the first satellite bag 41 and the third satellite bag 42. The control unit 50 may monitor the flow meter 72 to verify that the valves 63, 64 are operating correctly. Once a desired pressure is reached, valve 64 may be opened (S127), allowing the second supernatant plasma layer to flow through conduit 28 into the third satellite bag 42.

In S128 and S129, flow continues until a predetermined value or condition is reached, e.g., a sufficient amount of the second supernatant plasma layer has passed into satellite bag 42. This amount is preferably sufficient to collect much of the plasma without any of the platelets in the second sediment platelet containing layer passing into the third satellite bag 42. In accordance with a preferred embodiment of the invention, the amount of supernatant passing into the third satellite bag 42 is preferably predetermined based on weight or time, but it is intended that the invention should not be limited thereby.

In S130, after the predetermined amount of second supernatant plasma has been collected as determined by the control unit 50, in S128 and S129, valve 64 closes.

In S131, the pressure differential is shut off by the control unit 50, and the sequence is returned to the programmable initial sequence control.

In accordance with an additional embodiment of the invention, recovery of various biological fluids trapped or retained in various elements of the system is maximized, either by causing a volume of gas behind the trapped or retained biological fluid to push the fluid through those elements and into the designated container, assembly, or porous medium, or by drawing the trapped or retained fluid into the designated container, assembly, or porous medium by a pressure differential. This is accomplished automatically by the control unit by automatically controlling the various gas inlets or outlets 73–75, 81–82, 98, and 99. This provides for a more complete emptying of the container, assembly, or porous medium. Once the container is emptied completely, the flow may be stopped by the control unit 50 usually after a predetermined period of time has elapsed since the valve has been opened or closed.

While the invention has been described in some detail by way of illustration and example, it should be understood that the invention is susceptible to various modifications and alternative forms, and is not restricted to the specific embodiments set forth above. It should be understood that these specific embodiments are not intended to limit the invention but, on the contrary, the intention is to cover all modifications, equivalents, and alternatives falling within the spirit and scope of the invention.

What is claimed is:

1. A method for automatically processing a biological fluid comprising:

obtaining a container having a biological fluid therein;

providing a first signal and communicating with an automated control arrangement to establish flow of at least a portion of the biological fluid along a fluid flow path through a leukocyte depletion medium;

providing a second signal and communicating with the automated control arrangement to terminate flow along the fluid flow path, wherein providing the second signal includes sensing the back pressure in the fluid flow path through the leukocyte depletion medium.

2. The method of claim 1 wherein the leukocyte depletion medium comprises a fibrous medium.

3. The method of claim 1 wherein biological fluid in the container comprises at least a supernatant layer and a sediment layer, and the method includes establishing flow of at least a portion of the supernatant layer or the sediment layer through the leukocyte depletion medium.

4. The method of claim 3 comprising establishing flow of the supernatant layer through the leukocyte depletion medium.

5. The method of claim 3 comprising establishing flow of the sediment layer through the leukocyte depletion medium.

6. The method of claim 1 wherein establishing flow includes pressing against at least a portion of the container.

7. The method of claim 1 including passing gas from the container to a desired location.

8. The method of claim 7 including passing the gas to another container.

9. The method of claim 7 including passing gas through a gas outlet.

10. The method of claim 1 including placing the container having biological fluid therein in an enclosed housing.

11. The method of claim 1 including passing a platelet-containing biological fluid through the leukocyte depletion porous medium.

12. The method of claim 1 including passing a red blood cell-containing biological fluid through the leukocyte depletion porous medium.

13. A method for automatically processing a biological fluid comprising:

obtaining a container having a biological fluid therein;

supplying a first signal from an automated control arrangement to establish flow of at least a portion of the biological fluid along a fluid flow path through a leukocyte depletion medium;

supplying a second signal to the automated control arrangement to terminate flow along the fluid flow path, wherein supplying the second signal includes sensing the flow rate through the leukocyte depletion medium.

14. The method of claim 13 including passing gas from the container to a desired location.

15. The method of claim 14 including passing the gas to another container.

16. The method of claim 14 including passing gas through a gas outlet.

17. The method of claim 13 wherein the leukocyte depletion medium comprises a fibrous medium.

18. The method of claim 13 wherein biological fluid in the container comprises at least a supernatant layer and a sediment layer, and the method includes establishing flow of at least a portion of the supernatant layer or the sediment layer through the leukocyte depletion medium.

19. The method of claim 18 comprising establishing flow of the supernatant layer through the leukocyte depletion medium.

20. The method of claim 18 comprising establishing flow of the sediment layer through the leukocyte depletion medium.

21. The method of claim 13 wherein establishing flow includes pressing against at least a portion of the container.

22. The method of claim 13 including placing the container having biological fluid therein in an enclosed housing.

23. The method of claim 13 including passing a platelet-containing biological fluid through the leukocyte depletion porous medium.

24. The method of claim 13 including passing a red blood cell-containing biological fluid through the leukocyte depletion porous medium.

* * * * *